(12) United States Patent
Metzger et al.

(10) Patent No.: US 7,695,520 B2
(45) Date of Patent: Apr. 13, 2010

(54) PROSTHESIS AND IMPLEMENTATION SYSTEM

(75) Inventors: Robert Metzger, Wakarusa, IN (US); Duke A Fox, Winona Lake, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 828 days.

(21) Appl. No.: 11/444,268

(22) Filed: May 31, 2006

(65) Prior Publication Data

US 2007/0282451 A1 Dec. 6, 2007

(51) Int. Cl.
*A61F 2/38* (2006.01)
(52) U.S. Cl. .................................... 623/20.35
(58) Field of Classification Search ............. 623/20.21, 623/20.22, 20.35, 22.42
See application file for complete search history.

(56) References Cited

U.S. PATENT DOCUMENTS

| | | | |
|---|---|---|---|
| 1,763,730 A | 6/1930 | Von Lackum |
| 1,959,615 A | 5/1934 | Derrah |
| 2,433,815 A | 12/1947 | Laforge |
| 2,455,655 A | 12/1948 | Carroll |
| 2,702,550 A | 2/1955 | Rowe |
| 2,724,326 A | 11/1955 | Long |
| 2,955,530 A | 10/1960 | Nilo |
| 3,048,522 A | 8/1962 | Velley |
| 3,229,006 A | 1/1966 | Nohl |
| 3,514,791 A | 6/1970 | Sparks |
| 3,554,197 A | 1/1971 | Dobbie |
| 3,624,747 A | 11/1971 | McKnight |
| 3,631,596 A | 1/1972 | Glaus |
| 3,678,934 A | 7/1972 | Warfield et al. |
| 3,698,017 A | 10/1972 | Scales et al. |
| 3,703,036 A | 11/1972 | Karubian |
| 3,774,244 A | 11/1973 | Walker |
| 3,783,873 A | 1/1974 | Jacobs |
| 3,798,679 A | 3/1974 | Ewald |
| 3,807,393 A | 4/1974 | McDonald |
| 3,811,449 A | 5/1974 | Gravlee |
| 3,816,855 A | 6/1974 | Saleh |
| 3,837,009 A | 9/1974 | Walker |
| 3,840,905 A | 10/1974 | Deane |
| 3,852,830 A | 12/1974 | Marmor |
| 3,869,731 A | 3/1975 | Waugh et al. |
| 3,903,549 A | 9/1975 | Deyerle |

(Continued)

FOREIGN PATENT DOCUMENTS

CH 117960 5/1927

(Continued)

OTHER PUBLICATIONS

Vangaurd™ PFR, "Patellofemoral Arthroplasty, Consider the Other Compartment1" brochure, Biomet Orthopedics, Inc., 2005 (8 pages).

(Continued)

*Primary Examiner*—Bruce E Snow
*Assistant Examiner*—Melissa Montano
(74) *Attorney, Agent, or Firm*—Harness, Dickey

(57) ABSTRACT

A prosthesis for replacing a selected portion of the anatomy is disclosed. Also disclosed is an exemplary method and apparatus for performing a procedure. The procedure can be minimally or less invasive.

16 Claims, 15 Drawing Sheets

U.S. PATENT DOCUMENTS

| | | |
|---|---|---|
| 3,905,105 A | 9/1975 | Tuke |
| 3,905,374 A | 9/1975 | Winter |
| 3,911,923 A | 10/1975 | Yoon |
| 3,913,585 A | 10/1975 | Wolvek |
| 3,920,022 A | 11/1975 | Pastor |
| 3,941,127 A | 3/1976 | Froning |
| 3,967,625 A | 7/1976 | Yoon |
| 3,989,049 A | 11/1976 | Yoon |
| 3,991,426 A | 11/1976 | Flom |
| 3,994,287 A | 11/1976 | Turp |
| 4,053,953 A | 10/1977 | Flom |
| 4,055,862 A | 11/1977 | Farling |
| 4,081,866 A | 4/1978 | Upshaw et al. |
| 4,085,466 A | 4/1978 | Goodfellow |
| 4,085,743 A | 4/1978 | Yoon |
| 4,103,680 A | 8/1978 | Yoon |
| 4,178,641 A | 12/1979 | Grundei et al. |
| 4,299,224 A | 11/1981 | Noiles |
| 4,304,178 A | 12/1981 | Haberle |
| 4,311,145 A | 1/1982 | Esty |
| 4,344,193 A | 8/1982 | Kenny |
| 4,349,018 A | 9/1982 | Chambers |
| 4,373,709 A | 2/1983 | Whitt |
| 4,374,523 A | 2/1983 | Yoon |
| 4,385,404 A | 5/1983 | Sully |
| 4,386,609 A | 6/1983 | Mongeon |
| 4,400,833 A | 8/1983 | Kurland |
| D273,895 S | 5/1984 | Kenna |
| D274,091 S | 5/1984 | Kenna |
| 4,453,421 A | 6/1984 | Umano |
| 4,501,269 A | 2/1985 | Bagby |
| 4,509,518 A | 4/1985 | McGarry |
| 4,516,276 A | 5/1985 | Mittelmeier et al. |
| 4,545,375 A | 10/1985 | Cline |
| 4,554,686 A | 11/1985 | Baker |
| 4,562,598 A | 1/1986 | Kranz |
| 4,565,192 A | 1/1986 | Shapiro |
| 4,574,794 A | 3/1986 | Cooke et al. |
| 4,608,052 A | 8/1986 | Van Kampen et al. |
| 4,619,391 A | 10/1986 | Sharkany |
| 4,624,254 A | 11/1986 | McGarry |
| 4,641,648 A | 2/1987 | Shapiro |
| 4,642,120 A | 2/1987 | Nevo et al. |
| 4,662,372 A | 5/1987 | Sharkany |
| 4,678,470 A | 7/1987 | Nashef et al. |
| 4,682,598 A | 7/1987 | Beraha |
| 4,685,460 A | 8/1987 | Thornton |
| 4,711,233 A | 12/1987 | Brown |
| 4,718,413 A | 1/1988 | Johnson |
| 4,718,916 A | 1/1988 | Morscher |
| 4,739,751 A | 4/1988 | Sapega et al. |
| 4,794,854 A | 1/1989 | Swaim |
| 4,817,602 A | 4/1989 | Beraha |
| 4,822,365 A | 4/1989 | Walker et al. |
| 4,834,757 A | 5/1989 | Brantigan |
| 4,838,891 A | 6/1989 | Branemark et al. |
| 4,863,472 A | 9/1989 | Tormala et al. |
| 4,888,022 A | 12/1989 | Huebsch |
| 4,911,721 A | 3/1990 | Branemark et al. |
| 4,935,023 A | 6/1990 | Whiteside et al. |
| 4,936,852 A | 6/1990 | Kent |
| 4,950,296 A | 8/1990 | McIntyre |
| 4,952,213 A | 8/1990 | Bowman et al. |
| 4,961,740 A | 10/1990 | Ray et al. |
| 4,961,954 A | 10/1990 | Goldberg |
| 4,964,865 A | 10/1990 | Berkhead |
| 4,979,949 A | 12/1990 | Matsen, III et al. |
| 4,979,957 A | 12/1990 | Hodorek |
| 4,985,038 A | 1/1991 | Lyell |
| 5,007,912 A | 4/1991 | Albrektsson et al. |
| 5,015,247 A | 5/1991 | Michelson |
| 5,032,132 A | 7/1991 | Matsen |
| 5,060,678 A | 10/1991 | Bauman |
| 5,061,286 A | 10/1991 | Lyle |
| 5,062,843 A | 11/1991 | Mahony, III |
| 5,073,373 A | 12/1991 | O'Leary et al. |
| 5,082,670 A | 1/1992 | Gage et al. |
| 5,084,050 A | 1/1992 | Draenert |
| 5,092,869 A | 3/1992 | Waldron |
| 5,098,437 A | 3/1992 | Kashuba |
| 5,099,859 A | 3/1992 | Bell |
| 5,100,689 A | 3/1992 | Goldberg |
| 5,101,720 A | 4/1992 | Bianchi |
| 5,108,441 A | 4/1992 | McDowell |
| 5,111,987 A | 5/1992 | Moeinzadeh |
| 5,122,144 A | 6/1992 | Bert et al. |
| 5,123,906 A | 6/1992 | Kelman |
| 5,129,909 A | 7/1992 | Sutherland |
| 5,152,744 A | 10/1992 | Krause |
| 5,152,778 A | 10/1992 | Bales |
| 5,154,717 A | 10/1992 | Matsen, III et al. |
| 5,162,506 A | 11/1992 | Hadden |
| 5,163,949 A | 11/1992 | Bonutti |
| 5,170,800 A | 12/1992 | Smith |
| 5,171,243 A | 12/1992 | Kashuba |
| 5,171,244 A | 12/1992 | Caspari et al. |
| 5,171,276 A | 12/1992 | Caspari et al. |
| 5,174,300 A | 12/1992 | Bales |
| 5,176,702 A | 1/1993 | Bales |
| 5,178,622 A | 1/1993 | Lehner |
| 5,183,053 A | 2/1993 | Yeh |
| 5,183,464 A | 2/1993 | Dubrul |
| 5,186,178 A | 2/1993 | Yeh |
| 5,192,327 A | 3/1993 | Brantigan |
| 5,197,968 A | 3/1993 | Clement |
| 5,197,971 A | 3/1993 | Bonutti |
| 5,197,987 A | 3/1993 | Koch |
| 5,204,106 A | 4/1993 | Schepers et al. |
| 5,207,680 A | 5/1993 | Dietz et al. |
| 5,207,692 A | 5/1993 | Kraus |
| 5,217,463 A | 6/1993 | Mikhail |
| 5,226,916 A | 7/1993 | Goodfellow et al. |
| 5,228,459 A | 7/1993 | Caspari et al. |
| 5,234,433 A | 8/1993 | Bert et al. |
| 5,258,004 A | 11/1993 | Bales |
| 5,263,498 A | 11/1993 | Caspari et al. |
| 5,263,987 A | 11/1993 | Shah |
| 5,269,785 A | 12/1993 | Bonutti |
| 5,273,524 A | 12/1993 | Fox |
| D343,247 S | 1/1994 | Walen |
| 5,275,166 A | 1/1994 | Vaitekunas |
| 5,275,603 A | 1/1994 | Ferrante et al. |
| 5,282,803 A | 2/1994 | Lackey |
| 5,285,773 A | 2/1994 | Bonutti |
| 5,293,878 A | 3/1994 | Bales |
| 5,295,994 A | 3/1994 | Bonutti |
| 5,304,181 A | 4/1994 | Caspari et al. |
| 5,306,285 A | 4/1994 | Miller et al. |
| 5,308,349 A | 5/1994 | Mikhail |
| 5,312,411 A | 5/1994 | Steele et al. |
| 5,314,482 A * | 5/1994 | Goodfellow et al. ..... 623/20.35 |
| 5,322,505 A | 6/1994 | Krause |
| 5,329,846 A | 7/1994 | Bonutti |
| 5,342,367 A | 8/1994 | Ferrante et al. |
| 5,342,368 A | 8/1994 | Petersen |
| 5,344,423 A | 9/1994 | Dietz et al. |
| 5,344,458 A | 9/1994 | Bonutti |
| 5,348,541 A | 9/1994 | Lyell |
| 5,364,402 A | 11/1994 | Mumme et al. |
| 5,368,599 A | 11/1994 | Hirsch |
| 5,379,133 A | 1/1995 | Kirk |
| 5,382,249 A | 1/1995 | Fletcher |
| 5,383,937 A | 1/1995 | Mikhail |
| 5,390,683 A | 2/1995 | Pisharodi |

| Patent | Kind | Date | Inventor |
|---|---|---|---|
| 5,395,376 | A | 3/1995 | Caspari et al. |
| D358,647 | S | 5/1995 | Cohen |
| 5,425,355 | A | 6/1995 | Kulick |
| 5,425,745 | A | 6/1995 | Green |
| 5,445,639 | A | 8/1995 | Kuslich |
| 5,454,365 | A | 10/1995 | Bonutti |
| 5,454,815 | A | 10/1995 | Geisser |
| 5,454,816 | A | 10/1995 | Ashby |
| 5,456,268 | A | 10/1995 | Bonutti |
| 5,456,720 | A | 10/1995 | Schultz et al. |
| 5,472,415 | A | 12/1995 | King |
| 5,484,095 | A | 1/1996 | Green |
| 5,497,933 | A | 3/1996 | DeFonzo |
| 5,507,763 | A | 4/1996 | Petersen et al. |
| 5,514,139 | A | 5/1996 | Goldstein et al. |
| 5,514,143 | A | 5/1996 | Bonutti et al. |
| 5,520,692 | A | 5/1996 | Ferrante |
| 5,520,694 | A | 5/1996 | Dance et al. |
| 5,522,897 | A | 6/1996 | King |
| 5,540,695 | A | 7/1996 | Levy |
| 5,545,222 | A | 8/1996 | Bonutti |
| 5,549,683 | A | 8/1996 | Bonutti |
| 5,554,169 | A | 9/1996 | Green |
| 5,569,163 | A | 10/1996 | Francis |
| 5,570,700 | A | 11/1996 | Vogeler |
| 5,578,039 | A | 11/1996 | Vendrely et al. |
| 5,593,448 | A | 1/1997 | Dong |
| 5,597,379 | A | 1/1997 | Haines et al. |
| 5,609,603 | A | 3/1997 | Linden |
| 5,624,463 | A | 4/1997 | Stone |
| 5,632,745 | A | 5/1997 | Schwartz |
| 5,643,272 | A | 7/1997 | Haines et al. |
| 5,649,946 | A | 7/1997 | Bramlet |
| 5,653,714 | A | 8/1997 | Dietz et al. |
| 5,662,710 | A | 9/1997 | Bonutti |
| 5,667,069 | A | 9/1997 | Williams |
| 5,667,511 | A | 9/1997 | Vendrely et al. |
| 5,667,512 | A | 9/1997 | Johnson |
| 5,667,520 | A | 9/1997 | Bonutti |
| D385,163 | S | 10/1997 | Hutchins et al. |
| 5,681,316 | A | 10/1997 | DeOrio et al. |
| 5,683,398 | A | 11/1997 | Carls et al. |
| 5,694,693 | A | 12/1997 | Hutchins et al. |
| 5,702,447 | A | 12/1997 | Walch |
| 5,702,475 | A | 12/1997 | Zahedi |
| 5,704,941 | A | 1/1998 | Jacober et al. |
| 5,707,350 | A | 1/1998 | Krause |
| 5,712,543 | A | 1/1998 | Sjostrom |
| 5,716,360 | A | 2/1998 | Baldwin et al. |
| 5,718,708 | A | 2/1998 | Webb |
| 5,723,331 | A | 3/1998 | Tubo |
| 5,733,292 | A | 3/1998 | Gustilo et al. |
| 5,749,876 | A | 5/1998 | Duvillier et al. |
| 5,755,731 | A | 5/1998 | Grinberg |
| 5,755,791 | A | 5/1998 | Whitson |
| 5,755,803 | A | 5/1998 | Haines et al. |
| 5,769,855 | A | 6/1998 | Bertin et al. |
| 5,769,899 | A | 6/1998 | Schwartz |
| 5,772,594 | A | 6/1998 | Barrick |
| 5,788,700 | A | 8/1998 | Morawa et al. |
| 5,810,827 | A | 9/1998 | Haines et al. |
| 5,817,109 | A | 10/1998 | McGarry |
| 5,842,477 | A | 12/1998 | Naughton et al. |
| 5,846,931 | A | 12/1998 | Hattersley |
| 5,860,981 | A | 1/1999 | Bertin et al. |
| 5,866,415 | A | 2/1999 | Villeneuve |
| 5,871,493 | A | 2/1999 | Sjostrom |
| 5,879,354 | A | 3/1999 | Haines et al. |
| 5,888,219 | A | 3/1999 | Bonutti |
| 5,899,914 | A | 5/1999 | Zirps |
| 5,908,424 | A | 6/1999 | Bertin et al. |
| 5,911,723 | A | 6/1999 | Ashby et al. |
| 5,913,874 | A | 6/1999 | Berns |
| 5,916,219 | A | 6/1999 | Matsuno et al. |
| 5,921,990 | A | 7/1999 | Webb |
| 5,925,049 | A | 7/1999 | Gustilo et al. |
| 5,961,499 | A | 10/1999 | Bonutti |
| 5,997,566 | A | 12/1999 | Tobin |
| 6,007,537 | A | 12/1999 | Burkinshaw et al. |
| 6,012,456 | A | 1/2000 | Schuerch |
| 6,015,419 | A | 1/2000 | Strome |
| 6,019,767 | A | 2/2000 | Howell |
| 6,022,350 | A | 2/2000 | Ganem |
| 6,056,754 | A | 5/2000 | Haines et al. |
| 6,059,817 | A | 5/2000 | Bonutti |
| 6,059,831 | A | 5/2000 | Braslow et al. |
| 6,063,095 | A | 5/2000 | Wang et al. |
| 6,077,270 | A | 6/2000 | Katz |
| 6,077,287 | A | 6/2000 | Taylor |
| 6,086,593 | A | 7/2000 | Bonutti |
| 6,090,122 | A | 7/2000 | Sjostrom |
| 6,099,531 | A | 8/2000 | Bonutti |
| 6,099,532 | A | 8/2000 | Florea |
| 6,102,850 | A | 8/2000 | Wang et al. |
| 6,118,845 | A | 9/2000 | Simon et al. |
| 6,120,509 | A | 9/2000 | Wheeler |
| 6,132,472 | A | 10/2000 | Bonutti |
| 6,152,960 | A * | 11/2000 | Pappas .................. 623/20.31 |
| 6,156,070 | A | 12/2000 | Incavo et al. |
| 6,159,246 | A | 12/2000 | Mendes et al. |
| 6,165,221 | A | 12/2000 | Schmotzer |
| 6,171,340 | B1 | 1/2001 | McDowell |
| 6,174,321 | B1 | 1/2001 | Webb |
| 6,185,315 | B1 | 2/2001 | Schmucker et al. |
| 6,187,023 | B1 | 2/2001 | Bonutti |
| 6,195,168 | B1 | 2/2001 | De Lega |
| 6,197,064 | B1 | 3/2001 | Haines et al. |
| 6,198,794 | B1 | 3/2001 | Peshkin et al. |
| 6,211,976 | B1 | 4/2001 | Popovich et al. |
| 6,214,051 | B1 | 4/2001 | Badorf |
| 6,228,121 | B1 | 5/2001 | Khalili |
| 6,258,127 | B1 | 7/2001 | Schmotzer |
| 6,277,136 | B1 | 8/2001 | Bonutti |
| 6,290,703 | B1 | 9/2001 | Ganem |
| 6,290,704 | B1 | 9/2001 | Burkinshaw et al. |
| 6,325,806 | B1 | 12/2001 | Fox |
| 6,328,572 | B1 | 12/2001 | Higashida |
| 6,338,737 | B1 | 1/2002 | Toledano |
| 6,358,266 | B1 | 3/2002 | Bonutti |
| 6,361,565 | B1 | 3/2002 | Bonutti |
| 6,391,040 | B1 | 5/2002 | Christoudias |
| 6,406,495 | B1 | 6/2002 | Schoch |
| 6,409,722 | B1 | 6/2002 | Hoey |
| 6,423,063 | B1 | 7/2002 | Bonutti |
| 6,431,743 | B1 | 8/2002 | Mizutani |
| D462,767 | S | 9/2002 | Meyer |
| 6,468,280 | B1 | 10/2002 | Saenger et al. |
| 6,468,289 | B1 | 10/2002 | Bonutti |
| 6,478,799 | B1 | 11/2002 | Williamson |
| 6,482,209 | B1 | 11/2002 | Engh et al. |
| 6,500,181 | B1 | 12/2002 | Portney |
| 6,503,267 | B2 | 1/2003 | Bonutti et al. |
| 6,554,837 | B1 | 4/2003 | Hauri et al. |
| 6,554,838 | B2 | 4/2003 | McGovern et al. |
| 6,558,391 | B2 | 5/2003 | Axelson et al. |
| 6,575,982 | B1 | 6/2003 | Bonutti |
| 6,602,259 | B1 | 8/2003 | Masini |
| 6,620,181 | B1 | 9/2003 | Bonutti |
| 6,632,225 | B2 | 10/2003 | Sanford et al. |
| 6,635,073 | B2 | 10/2003 | Bonutti |
| 6,673,077 | B1 | 1/2004 | Katz |
| 6,676,662 | B1 | 1/2004 | Bagga et al. |
| 6,695,848 | B2 | 2/2004 | Haines |
| 6,702,821 | B2 | 3/2004 | Bonutti |
| 6,770,078 | B2 | 8/2004 | Bonutti |
| 6,893,467 | B1 * | 5/2005 | Bercovy .................. 623/20.14 |

| | | |
|---|---|---|
| 2001/0034554 A1 | 10/2001 | Pappas |
| 2001/0037155 A1 | 11/2001 | Merchant |
| 2002/0029038 A1 | 3/2002 | Haines |
| 2002/0029045 A1 | 3/2002 | Bonutti |
| 2002/0052606 A1 | 5/2002 | Bonutti |
| 2002/0116023 A1 | 8/2002 | Fletcher et al. |
| 2002/0173797 A1 | 11/2002 | Van Zile et al. |
| 2002/0198529 A1 | 12/2002 | Masini |
| 2002/0198531 A1 | 12/2002 | Millard et al. |
| 2003/0028196 A1 | 2/2003 | Bonutti |
| 2003/0060831 A1 | 3/2003 | Bonutti |
| 2003/0100906 A1 | 5/2003 | Rosa et al. |
| 2003/0100907 A1 | 5/2003 | Rosa et al. |
| 2003/0130665 A1 | 7/2003 | Pinczewski et al. |
| 2003/0153923 A1 | 8/2003 | Pinczewski et al. |
| 2003/0171757 A1 | 9/2003 | Coon et al. |
| 2003/0181984 A1 | 9/2003 | Abendschein |
| 2003/0212403 A1 | 11/2003 | Swanson |
| 2003/0216741 A1 | 11/2003 | Sanford et al. |
| 2003/0220641 A1 | 11/2003 | Thelen et al. |
| 2003/0225413 A1 | 12/2003 | Sanford et al. |
| 2003/0225457 A1 * | 12/2003 | Justin et al. ............... 623/20.14 |
| 2004/0039395 A1 | 2/2004 | Coon et al. |
| 2004/0102785 A1 | 5/2004 | Hodorek et al. |
| 2004/0138670 A1 | 7/2004 | Metzger |
| 2005/0113840 A1 | 5/2005 | Metzger et al. |
| 2005/0149042 A1 | 7/2005 | Metzger |
| 2005/0203533 A1 | 9/2005 | Ferguson et al. |
| 2006/0142774 A1 | 6/2006 | Metzger |

FOREIGN PATENT DOCUMENTS

| | | |
|---|---|---|
| DE | 337437 | 5/1921 |
| FR | 1111677 | 3/1956 |
| FR | 2758715 | 7/1998 |
| JP | 64-29266 | 1/1989 |
| WO | WO96/07361 | 3/1996 |
| WO | WO97/29703 | 8/1997 |

OTHER PUBLICATIONS

"AGC 3000 Intramedullary Surgical Technique Using PMMA Fixation," 1987, Biomet, Inc.

"AGC Total Knee System, Intramedullary Without Distractor Surgical Technique," 1989, Biomet, Inc.

"AGC-S Total Knee System, Surgical Technique for the AGC-S Total Knee System," 1992, Biomet, Inc.

"Anatomic Axial Alignment Instrumentation," 1994, Biomet, Inc.

"The AGC Revision Knee System Surgical Technique," 1997, Biomet, Inc.

Biomet Orthopedics, Inc., "Microplasty Minimally Invasive Knee Instruments," 2004, pp. 1-12.

Biomet Orthopedics, Inc., The Oxford™, brochure entitled "Unicompartmental Knee System", Jul. 15, 2004.

Biomet, Inc. "AGC Distal Fem Cutter for Dr. Hardy", Jun. 22, 1989.

Biomet, Inc., Genus™, brochure entitled "Uni Knee System", Nov. 15, 1998.

Install/Burstein II Modular Knee System by Zimmer, Inc., Copyright 1989.

Keys, Graham W., "Reduced Invasive Approach for Oxford II Medial Unicompartmental Knee Replacement—A Preliminary Study," The Knee (1999) pp. 193-196.

MIS Minimally Invasive Solution—The M/G Unicompartmental Knee by Zimmer, 4 sheets.

MIS Minimally Invasive Solution The M/G Unicompartmental Knee Minimally Invasive Surgical Technique, by Zimmer, Copyright 2000.

NexGen Complete Knee Solution—Extramedullary/Intramedullary Tibial Resector Surgical Technique—Publication date unknown, but before Aug. 1, 2001.

NexGen Complete Knee Solution—Intramedullary Instrumentation Surgical Technique—For the NexGen Cruciate Retaining & Legacy Posterior Stabilized Knee—Publication date unknown, but before Aug. 1, 2001.

NexGen Complete Knee Solution—Multi-Reference 4-in-1 femoral Instrumentation—Anterior Reference Surgical Technique—Publication date unknown, but before Aug. 1, 2001.

NexGen Complete Knee Solution—Surgical Technique for the LPS-Flex Fixed Bearing Knee—Publication date unknown, but before Aug. 1, 2001.

NexGen System Complete Knee Solution—Design Rationale—Publication date unknown.

Operative Arthroscopy—John B. McGinty, M.D.—Department of Orthopaedic Surgery, Medical University of South Carolina, Charleston, South Carolina—copyright 1991 by Raven Press, Ltd. p. 9.

Scorpio! Single Axis Total Knee System—Passport Total Knee Instruments—Passport A.R. Surgical Technique by Stryker Howmedica Osteonics, Copyright 2000.

Simple Instruments Surgical Technique for the Knee, copyright 2000 Biomet, Inc.

Surgical Navigation for Total Knee Arthroplasty—Believed to have been presented at the American Academy of Orthopedic Surgeons in Feb. 2001.

* cited by examiner

PROSTHESIS AND IMPLEMENTATION SYSTEM

FIELD

The present disclosure relates generally to a method and apparatus for performing an orthopedic procedure, and particularly to a method and apparatus and prosthesis for a distal femoral procedure.

BACKGROUND

The statements in this section merely provide background information related to the present disclosure and may not constitute prior art.

Generally, portions of the anatomy, such as a human anatomy, include bony portions that can articulate relative to one another in joints. At the joints, the articulations provide movement of the various bony portions relative to one another to allow for movement of the anatomy and mobility thereof. For example, a femur can articulate with a tibia at a knee joint to allow for movement of the legs of an anatomy.

The natural anatomy generally allows for substantially smooth and pain free articulation at the various joints in the anatomy. For various reasons, such as injury, disease, and for other reasons, the articulations may become damaged or painful. The damaged articulations, in certain circumstances, can be replaced to substantially return the anatomy to its natural articulation.

To perform a procedure to allow for natural articulation to replace a damaged joint, it may be desirable to substantially minimize the amount of intrusion of the soft tissue surrounding the joint. Such reduced invasive procedure can be desirable to achieve various results. Therefore, it is desirable to provide a prosthesis and system allowing for implantation of a prosthesis in a substantially less invasive manner.

SUMMARY

A method and apparatus is disclosed for performing a procedure on a portion of the anatomy, for example, in a knee including a distal femoral portion, to prepare a portion of the anatomy for an implantation. The preparation of the distal femur, for example, can include resecting various portions of the distal femur to prepare it for implantation of a prosthesis. Also disclosed is a prosthesis that is provided to interconnect with the prepared portions of the anatomy, such as the distal femoral portion, in a selected manner.

The method and apparatus for preparing the distal femur can be used in a substantially less invasive or minimally invasive procedure to reduce trauma to soft tissue surrounding the distal femur. Also natural and/or healthy bone can be conserved during implantation. Likewise, alternative instruments and methods can be used for preparing an anatomy for implantation. For example, a posterior chamfer resection can be avoided with selected milling systems and techniques disclosed herein.

The prosthesis can also be provided to interconnect with the distal femur after preparation of the distal femur in a less invasive manner. The prosthesis can be provided to interconnect with the femur in a substantially complete contact with the femur to allow for an efficient transfer of forces through the prosthesis to the femur.

According to various embodiments a prosthesis for positioning in a selected portion of an anatomy is disclosed. The prosthesis can include a first portion defining a substantially planar surface operable to fixedly engage a first surface of the anatomy. The prosthesis can also include a second portion defining a curved surface operable to engage a second surface of the anatomy. The prosthesis can be formed from one or more pieces.

According to various embodiments a system for positioning a prosthesis relative to a selected portion of an anatomy is disclosed. The system can include a mill operable to mill the anatomy and a mill guide operable to guide the mill relative to the anatomy. A mill guide placement system can also be provided to assist in a positioning of the mill guide. Further, an alignment instrument operable to align at least one of the mill guide, the mill guide placement system, or combinations thereof relative to the anatomy can be provided and used.

According to various embodiments, a method of positioning a prosthesis relative to a bone in an anatomy is disclosed. The method can include forming a first curved surface on a first portion of the bone and forming a planar surface on the bone. An implant can be positioned to mate, in a selected manner, with the first curved surface and the planar surface.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION OF VARIOUS EMBODIMENTS

Figure 1:
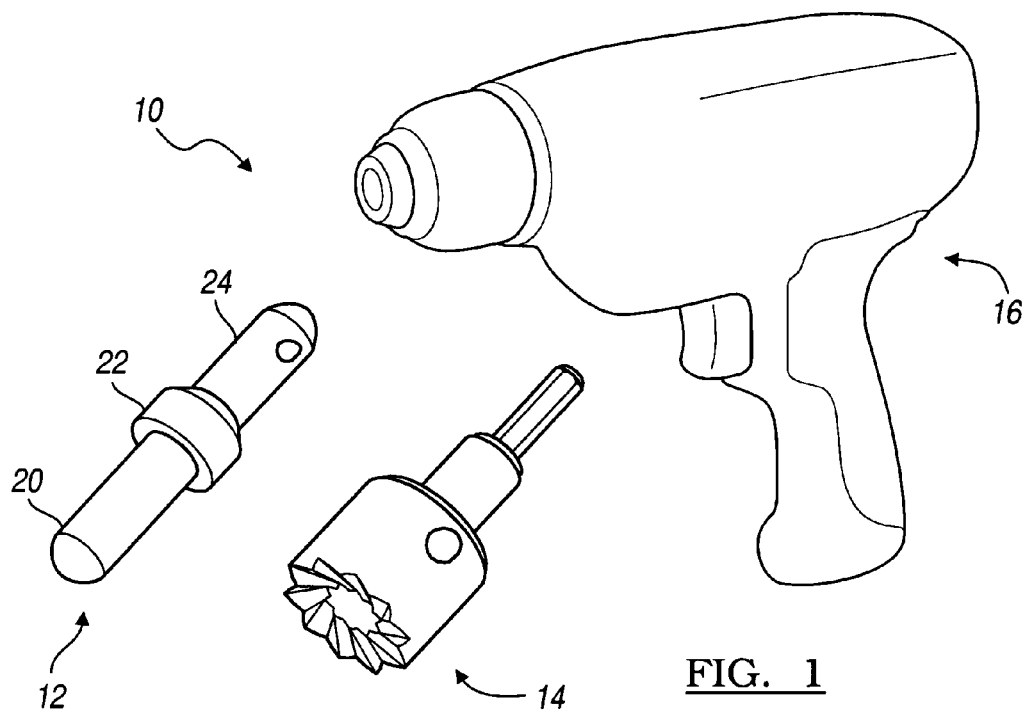
FIG. 1 is an exploded plan of view of an instrument assembly according to various embodiments.

The following description is merely exemplary in nature and is not intended to limit the present disclosure, application, or uses. It should be understood that throughout the drawings, corresponding reference numerals indicate like or corresponding parts and features.

With reference to FIG. 1, a milling apparatus or system 10, can include a spigot or mill guide portion 12, a mill portion 14, and a drill motor or driver 16. The drill motor or driver 16 can be any appropriate driver such as pneumatic, electric, air powered, manual powered, or the like. The drill motor 16 can be any commonly used drill motor for a surgical procedure that is able to be sterilized, re-used, or single use. The mill portion 14 can be any appropriate mill, such as the mill used with the Oxford® Unicompartmental Knee™ provided by Biomet, Inc. of Warsaw, Ind. The mill 14 can be provided to interconnect with the drill motor 16 in any appropriate manner such as with a chuck, a quick connect, or the like. The mill 14 generally provides for milling a selected portion of the anatomy, such as a distal portion of the femur, described further herein. Nevertheless, the mill 14 usually can be formed to provide a selected mill surface, such as a substantially convex milled surface on the femur or bone portion milled with the mill 14. Therefore, the mill 14 can include a concave milling surface or tooth structure. A plurality of cutting teeth 18 can be provided on the mill 14 to mill or resect a selected bone portion in an appropriate manner. It will be understood, however, that the mill 14 can be formed in any appropriate manner to achieve a selected result. For example, the mill can be provided to form a flat surface on the distal femur, a concave surface on the distal femur, or any other appropriate shape or cross-section. One skilled in the art will understand that mills can be formed in different and appropriate shapes to provide a shaped milled surface.

Also, the spigot 12 can include various portions to interconnect with selected portions of the anatomy. For example, an insertion end 20 can be inserted into a selected portion of the anatomy, such as a distal portion of the femur, a stop area or member 22 can ensure that a selected guide portion 24 extends from the selected bony portion, such as the femur. Also a plurality of spigots 12 can be provided, each having a different length distal end. The different lengths can assist in selections on amount of bone to resect.

The milling assembly 10 can be provided in any appropriate manner for a selected procedure. It will be understood that the milling assembly 10 can be provided with each and every piece, also, various pieces can be reusable, or single use. Further, the mill 14 can be provided in a plurality of sizes depending upon a selected procedure, patient, or the like. Further, the guide 12 can be provided in various different sizes, lengths, diameters, etc., for different procedures or different patients.

Figure 2:
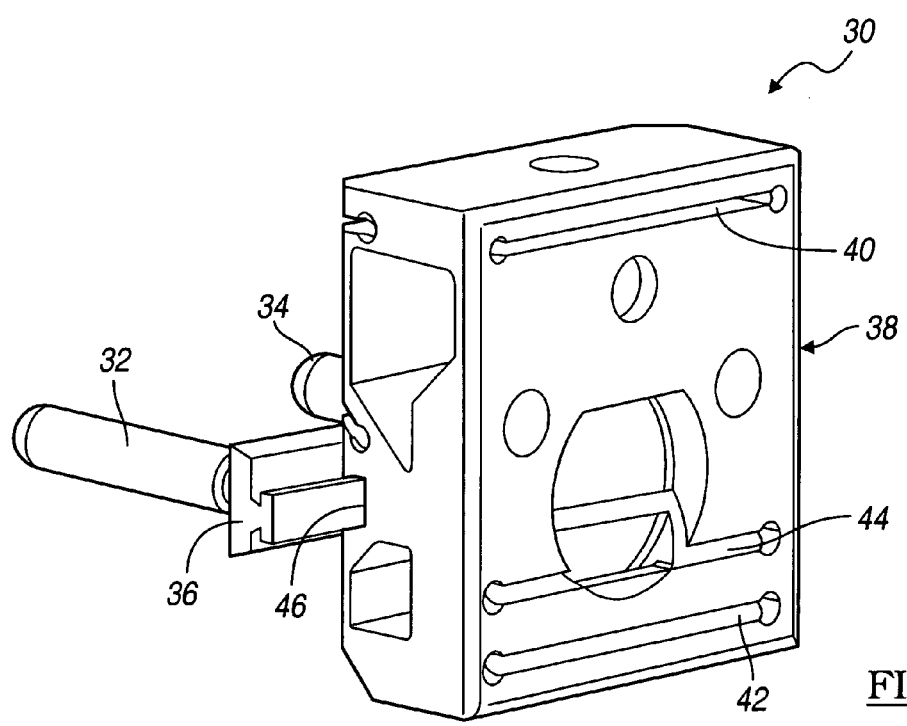
FIG. 2 is a perspective view of a guide block according to various embodiments.
Figure 3A:
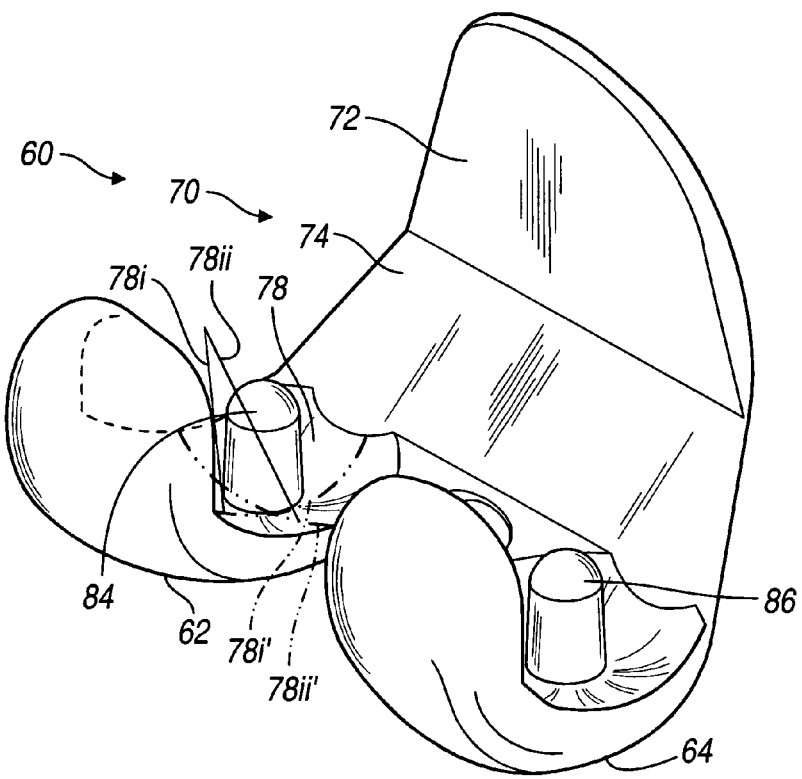
FIG. 3A is a perspective back view of a prosthesis according to various embodiments.
Figure 3B:
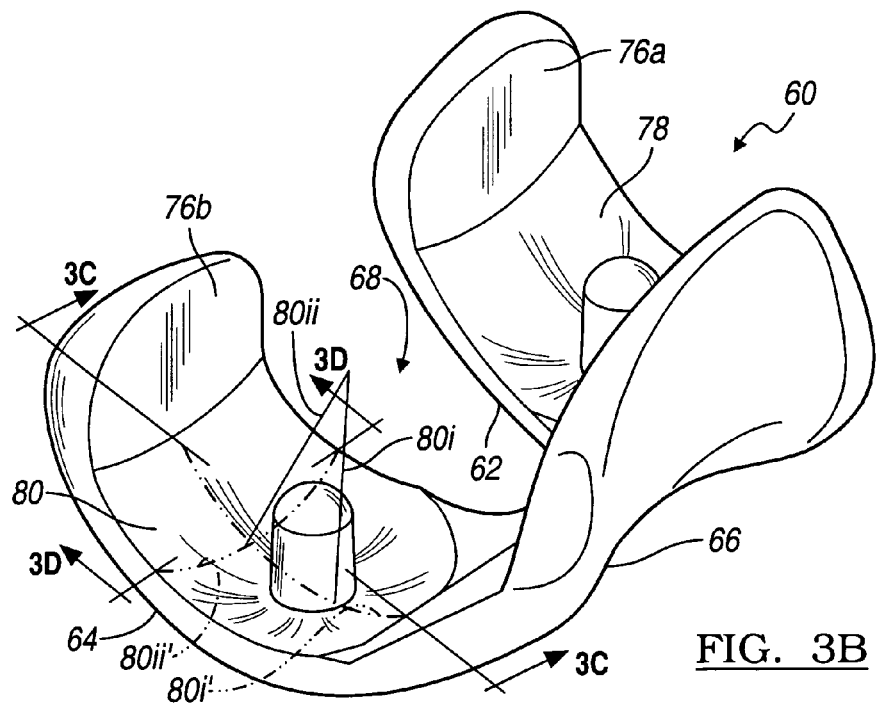
FIG. 3B is a perspective top view of a prosthesis according to various embodiments.
Figure 3C:
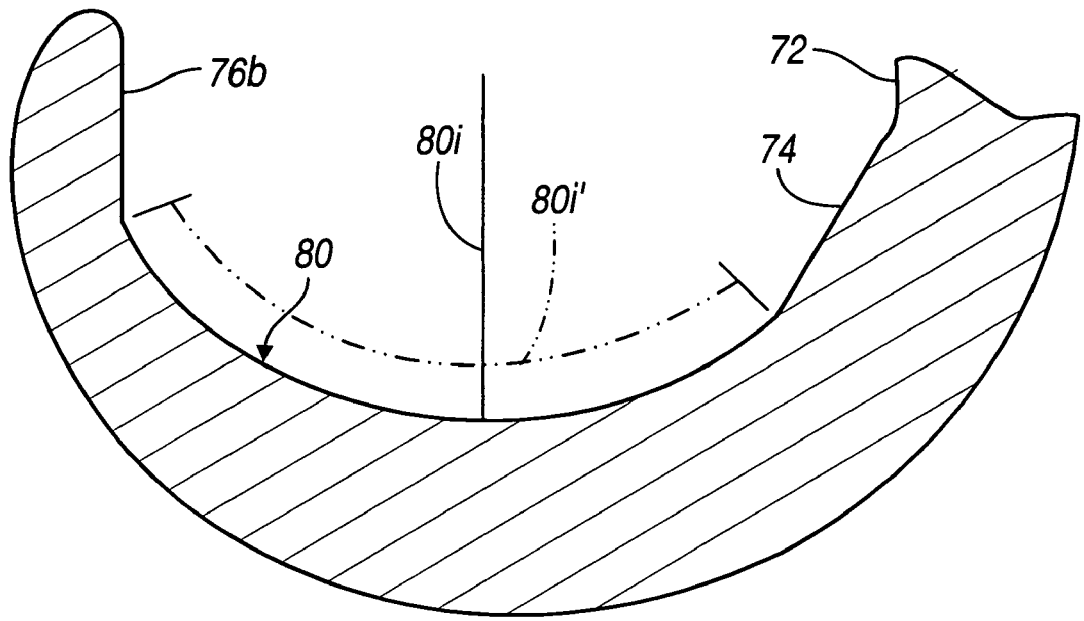
FIG. 3C is a cross-section view along line 3C-3C from FIG. 3B.
Figure 3D:
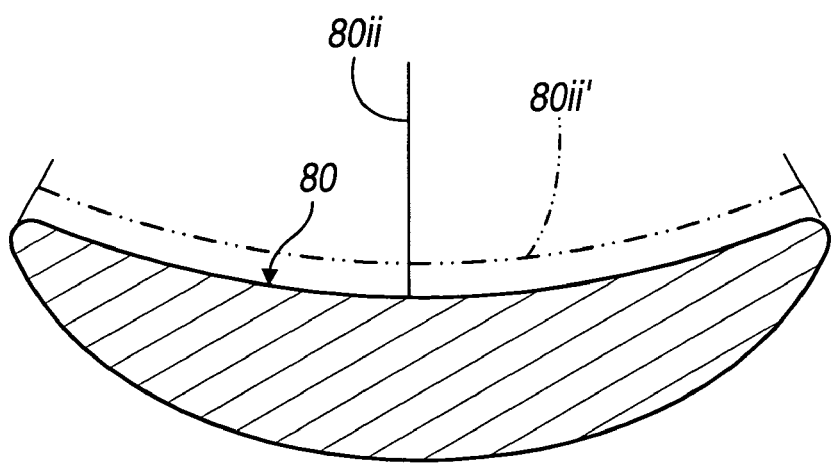
FIG. 3D is a cross-section view along line 3D-3D from FIG. 3B.

With reference to FIG. 2, a guiding block or cutting block 30 is illustrated. The guide block 30 can be any appropriate guide block such as the guide block disclosed in U.S. patent application Ser. No. 11/337,861, filed on Jan. 23, 2006, commonly assigned, and incorporated herein by reference. Briefly, the guide block assembly 30 can include a bone engagement portion, such as a first pin 32 and a second pin 34, a rail 36 and a cutting guide block 38.

The cutting block assembly 30 can be interconnected with any appropriate bone apportion, such as a distal portion of a femur. When interconnected with the distal portion of a femur, the cutting guide block 38 can be used to make various cuts. For example, the cutting guide block 38 can include a first guide slot 40 to form an anterior cut on a femur. The cutting guide block 38 can also include a second guide slot or surface 42 to form a posterior cut and the guide lock 38 can include a third guide slot 44 to form an anterior chamfer cut. The various guide slots 40-44 can be used to resect a bone, such as the femur, to interconnect with a selected portion. It will be understood, however, that the guide block 38 can also include various other guide passages or slots, such as to form a posterior chamfer cut, medial or lateral cuts, or any appropriate portion.

Further, the guide block 38 can be formed to move relative to the tract 36 as is taught in the previously incorporated application. The cutting block 38 can define an articulation portion 46 which articulates with a portion of the rail 36 to allow the cutting block 38 to slide relative to the rail 36. The cutting block 38 can then be formed at any appropriate size, such as about three centimeters to about six centimeters in width, or any other appropriate size. The cutting block assembly 30 can be interconnected with a bone portion in any appropriate manner, such as those described further herein. Also, the various slots 40-44, can be used to guide instruments, such as a saw blade, relative to a portion to which the guide assembly 30 is attached.

With reference to FIGS. 3A to 3D, a prosthesis 60 is illustrated. The prosthesis 60 can be any appropriate prosthesis, such as a distal femoral prosthesis. The prosthesis 60 is exemplary illustrated as a distal femoral prosthesis, but the various features and portions thereof can be incorporated on any selected implant assemblies. Also, the prosthesis 60 is exemplary a cruciate retaining prosthesis, but it can also be a posterior stabilized, constrated, or any combination thereof.

The prosthesis 60 can include various portions to replace or mimic the distal femoral portion. For example, the prosthesis 60 can include a first condyle portion 62 and a second condyle portion 64. The condyle portions 62, 64 can replace the medial and lateral condyles of a distal portion of a femur. It will be understood that the condyle 62, 64 can be any appropriate condyle portion such as the medial or lateral condyle portion, and is exemplary listed here only.

The condyle portions 62, 64 can interconnect and be formed as a single piece with a patellar tract portion 66. The patellar tract portion 66 can allow a place for articulation of a patella, either natural or prosthetic patella, once the prosthesis 60 is implanted onto the distal femoral portion. The condyle 62, 64 and patellar tract 66 can generally define an exterior portion of the prosthesis 60. The exterior portion of the prosthesis can be substantially curved, either continuously or discontinuously, to replace a distal femoral portion. Further, it will be understood that the prosthesis 60 can define an opening or passage 68 between the two condyles 62, 64. Alternatively, according to various embodiments, the prosthesis 60 can define a substantially solid portion between the condyle 62, 64 for various reasons, such as a particular patient, a particular application, or the like. Also the prosthesis 60 can be formed from many pieces and be interconnected prior to implantation, during implantation, or at any appropriate time.

The prosthesis 60 can further define a bone contacting or interior surface 70. The interior surface 70 can be substantially smooth, can be porous, or any combination thereof. It will be understood that a porous portion, such as a porous coating, can be applied to the interior surface 70 of the prosthesis 60 to allow for bone ingrowth, adhesive adhesion, or the like. Regardless, the interior surface 70 can include various portions.

A first portion of the interior 70 can be a substantially anterior surface 72. The anterior surface can be substantially flat and formed an angle relative to a second portion 74. The anterior surface 72 can be provided to contact an anterior portion of a distal femur, as illustrated herein. The second surface 74 can be a portion that is operable to contact an anterior chamfer portion, such as an anterior chamfer cut, formed on a distal femur. The first surface 72 and the second surface 74 can be formed at any appropriate angle relative to one another, and can depend upon an anatomy of the patient, a characteristic of the prosthesis, or any appropriate reason. A third surface can be a substantially posterior surface 76a and 76B. The posterior surfaces 76a, 76b, can be provided as two surfaces, as illustrated here when the space 68 is formed or it can be a substantially single surface that is continuous along the width of the prosthesis 60. Nevertheless, the posterior surfaces 76a, 76b can be formed to contact a posterior portion of the femur as illustrated herein.

The interior surface of a substantial portion of the condyle, 62, 64 can be substantially curved. A first curved surface 78 can be formed opposite the first condyle 62 and a second curved surface 80 can be formed opposite the second condyle 64. The curved surfaces 78, 80 can be curved relative to the other surfaces of the interior portion 70 of the prosthesis 60. The curved surface 80 is exemplary illustrated in FIGS. 3C and 3D, but curved surface 78 can be similarly illustrated.

The first curved surface 78 can include a substantially anterior to posterior curvature that includes a first radius 78i that can be used to form an arc 78i'. A second radius 78ii can define a second medial to lateral arc 78ii'. The two arcs 78i' and 78ii' can define two curved surfaces or two radii that define the curved surface 78. The curved surface of 78 can contact a selected portion of the anatomy, such as a prepared distal femur, as discussed further herein.

The second curved surface 80 can include similar portions. For example, a first radius 80i can define an arc 80i' similar to the arc 78i'. Also, a second radius 80ii can define a second arc 80ii' that is similar to the second arc 78ii'. As discussed above, the curved surface 80 is exemplary illustrated in detail in FIGS. 3C and 3D but curved surface 78 can be understood to be similar to curved surface 80.

The curved surfaces 78, 80 can be formed on the prosthesis 60 in any appropriate manner, such as by milling, casting, or any other appropriate formation procedure. Further, the various other surfaces defined by the interior 70 of the prosthesis 60 can be formed in any appropriate manner such as milling or casting.

As discussed above, the prosthesis 60 can be interconnected with a portion of the anatomy, such as the distal portion of the femur, in any appropriate manner. Further, the prosthesis 60 can define a first projection 84 and a second projection 86. The projections 84, 86 can project into a selected portion of the anatomy, such as a distal portion of the femur, to assist in interconnecting the prosthesis 60 with the anatomy. The projections 84, 86 can be formed in any appropriate manner and can be formed as a single piece with the prosthesis 60, formed separately and integrated therewith, or provided in any appropriate manner. The projections 84, 86 can also include a substantially smooth or porous surface, or combinations thereof. As discussed above, a porous surface can assist with bone ingrowth, adhesive adhesion, or any other appropriate purpose.

Figure 4:
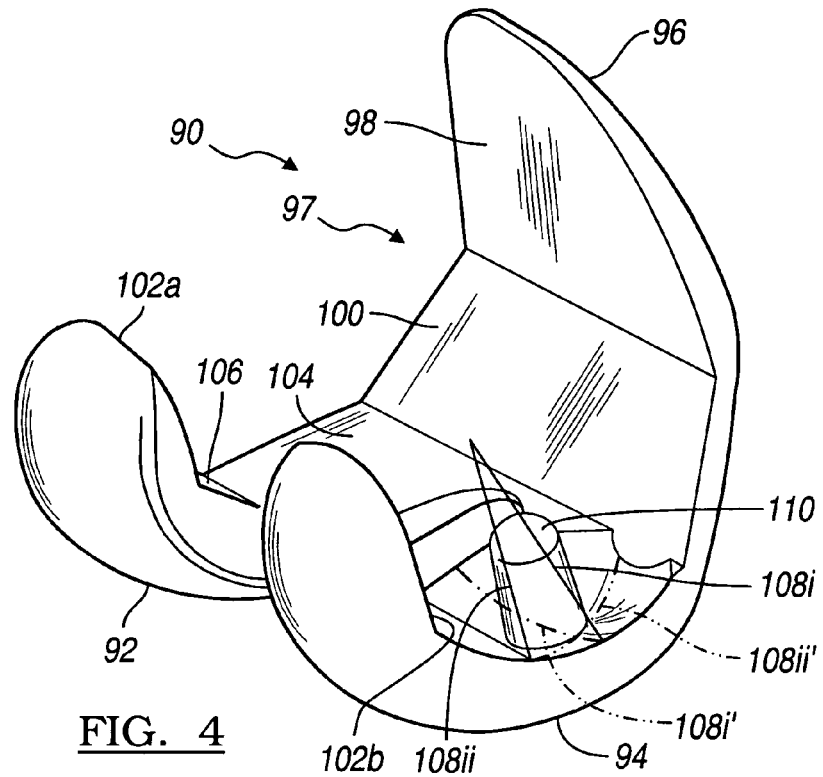
FIG. 4 is a perspective back view of a prosthesis according to various embodiments.

With reference to FIG. 4, a prosthesis 90, according to various embodiments, is illustrated. The prosthesis 90 can include portions substantially similar to the prosthesis 60. Therefore the prosthesis 90 can include an exterior surface that defines a first condyle and second condyles 92, 94 substantially similar to the first and second condyles 62, 64 of the prosthesis 60. Also the prosthesis 90 can define a patellar tract 96 similar to the patellar tract 66 in the prosthesis 60. An internal surface of the prosthesis 90 can also include a first substantially planar section 98 and a second substantially planar section 100. A third section 102a and 102b can include a posterior portion similar to the posterior portions 76a, 76b of the prosthesis 60.

The interior surface 97 can include portions that are dissimilar on an interior portion opposite the condyles 92, 94. For example, the interior surface opposite the first condyle 92 can includes substantially planar sections such as a distal planar section 104 and a posterior chamfer planar section 106. The distal internal section 104 can be placed at an angle relative to the posterior chamfer section 106 in a manner substantially similar to prosthesis generally available, just as the Ascent® prosthesis provided by Biomet, Inc. of Warsaw, Ind.

The interior surface opposite the second condyle 94, however, can be curved similar to the curvature of the interior portions of the prosthesis 60. Therefore, the interior surface opposite the second condyle 94 can include a first radius 108i that defines an arc 108i' in a generally medial to lateral direction. Also, as discussed above the curved surface of the interior of the condyle 94 can be similar to the curved surface 80 illustrated in FIGS. 3C and 3D. A second radius 108ii' can define a second arc 108ii' in a generally anterior to posterior direction. Therefore, the interior surface opposite the second condyle 94 can be curved substantially similar to the curvature 78, 80 of the prosthesis 60. Further, a projection or post 110 can extend from the second surface opposite the second condyle 94 and can also optionally be provided to extend from the distal planar portion 104.

It will be understood that the prosthesis 90, according to various embodiments, can include an interior surface that includes both a curved portion and a substantially planar portion. The prosthesis 90 need not include a substantially symmetrical interior surfaces. The interior of the prosthesis 90 can be based upon the process of forming the distal femoral portion or any appropriate bony portion. The prosthesis 90 can be provided for a formation of a distal femur that can have a substantially curved facing portion for one condyle and a planar portion for a second condyle.

Distal femoral prostheses, such as the prosthesis 60 and the prosthesis 90 can be implanted according to any appropriate method and with the assistance of any appropriate instruments. For example, the bone portion, such as a distal portion of the femur, can be resected or prepared according to a plurality of steps, such as milling. To ensure that the several steps are appropriately aligned for positioning the prosthesis relative to the femur, various instruments can be used to assist the procedures. It will be understood that the instruments and method described herein are merely exemplary.

Figure 5:
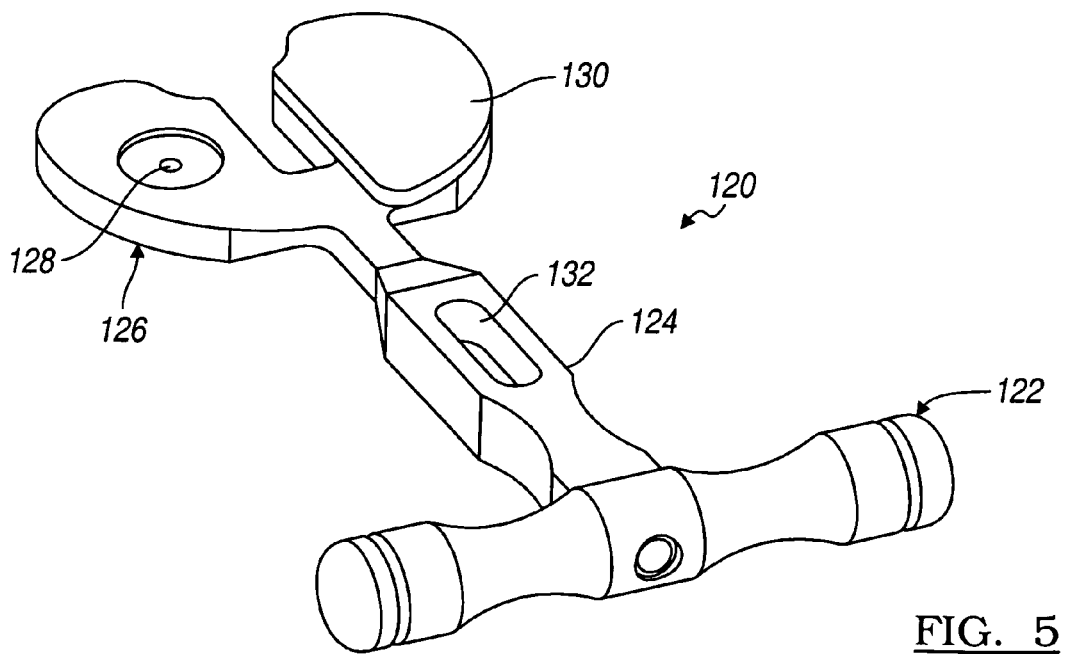
FIG. 5 is a perspective top view of an alignment instrument according to various embodiments.

With reference to FIG. 5, an alignment tool 120 is illustrated. The alignment tool 120 can be any appropriate alignment tool, including that illustrated in FIG. 5 and described in currently pending U.S. patent application Ser. No. 11/444,270, concurrently filed and incorporated herein by reference. The alignment tool 120 can be used to ensure that appropriate resections cut in one bone are aligned relative to one another and/or aligned to portions of adjacent bones.

Briefly, the alignment tool 120 can include a graspable portion 122 and extension arm 124 and a spacer portion or alignment portion 126. The alignment portion 126 can include a connection mechanism 128 to interconnect with a connection mechanism of a spacer member 130. The spacer member 130 can include a plurality of spacer members of different heights, or other appropriate dimensions, to be interconnected with the alignment portion 126. The spacer members 130 can be interconnected, such as with a snap fit, to the connection mechanism 128 of the alignment portion 126. As discussed herein, the alignment portion 126 can include the spacers 130 to assist in assuring appropriate alignment or spacing between various portions of the bone.

The extension arm 124 can include a passage or define a passage 132 through which an alignment rod can pass. As discussed herein, an alignment rod can be used to ensure appropriate alignment of the various bones relative to one another when various resections are aligned relative to one another with the alignment portion 126.

Figure 6A:
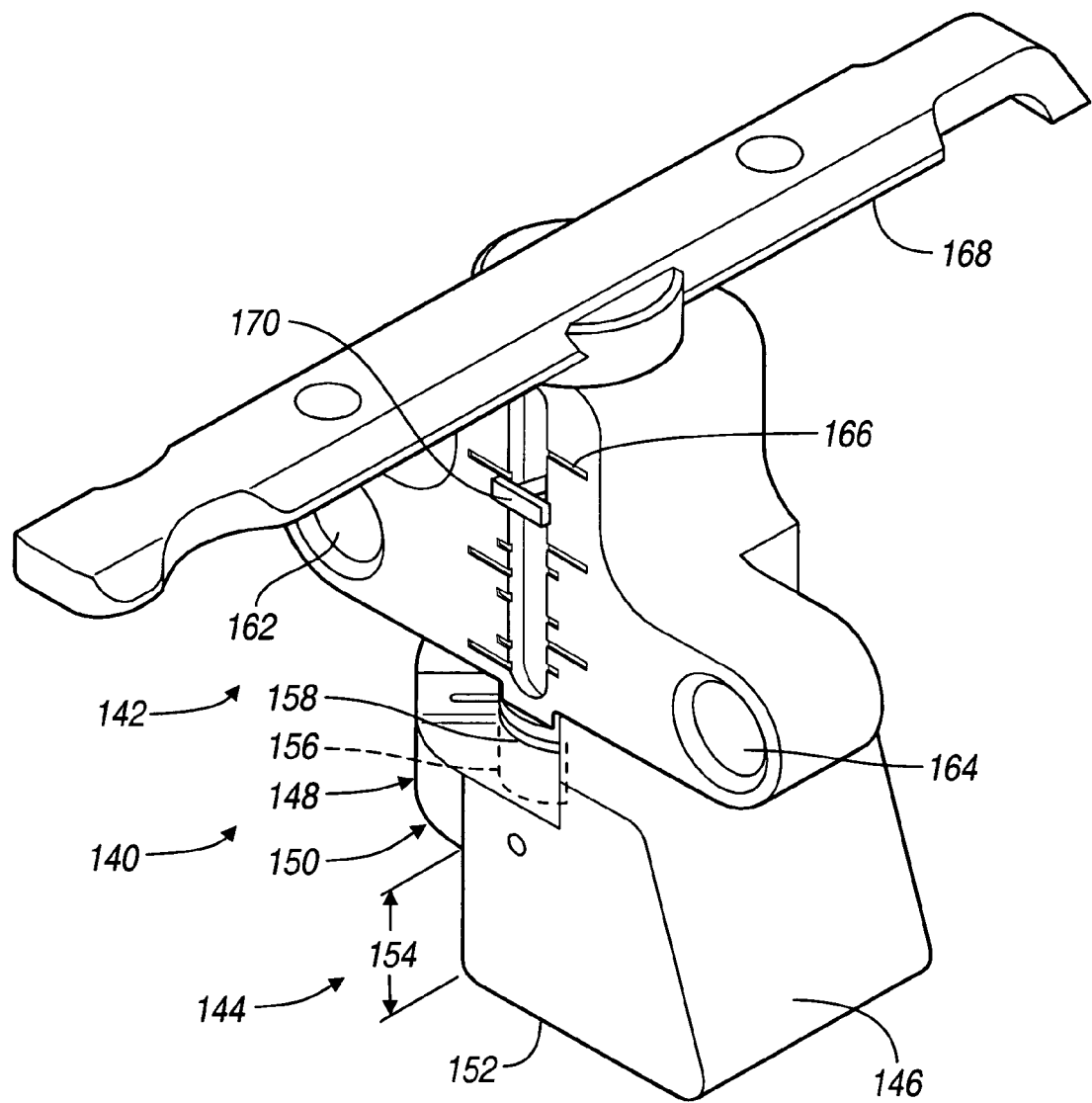
FIG. 6A is a perspective front view of a sizing instrument according to various embodiments.

With reference to FIG. 6A, a sizer 140 is illustrated. The sizer 140 can be used to select or obtain an appropriate size for an implant member to be positioned relative to a selected bone. The sizer 140 can be an anterior posterior (AP) sizer. This can ensure that the anterior to posterior distance of the second bone, such as the femur, is appropriate.

The AP sizer 140 can include two general portions, including a first guide portion 142 and a second base portion 144. The base portion 144 can include a first side 146 that includes a selected dimension that is larger than a second side 148. The first side relative to the second side can allow it to rest upon a selected instrument, such as the alignment guide 120 to reference relative to the alignment guide 120. From a lower or bottom surface 150 of the second side to a lower bottom surface 152 of the first side can be any appropriate dimension such as a dimension 154. The dimension 154 can be any appropriate dimension such as about 2 mm to about 10 mm. Regardless, the dimension 154 can generally allow the sizer 140 to rest upon the guide 120 regardless of the differential between the various spacer members 130 are interconnected with the alignment surface 126. In this way, the referencing for the guide portion 142 can be from the lower side of the alignment instrument 120.

The base portion 144 can interconnect with the guide portion 142 in a rotational manner so that the taller side can contact the lowest portion of the alignment tray 126. The base portion 144 can define a bore 156 which can rotationally receive a spindle 158 of the guide portion 142. This can allow the guide portion 142 to rotate relative to the base portion 144. It will be understood that any appropriate mechanism will be used or provided to interconnect or selectively lock the base portion 144 relative to the guide portion 142. For example, a quick release mechanism can be provided which can include a member biased in a selected direction by a spring that can selectively engage and disengage to interconnect the base portion 144 relative to a selected orientation of the guide portion 142.

The guide portion 142 can include any appropriate portions. For example, the guide portion 142 can include or define a first passage 162 and a second guide passage 164. The guide passages 162, 164 can be used to guide a selected instrument, such as a drill point, relative to a selected portion, such as a portion of a bone. The guide passages 162, 164 can be any appropriate size or dimension relative to one another to achieve a selected result.

The guide portion 142 can also include a scale marking 166 to allow for determining of a selected dimension. As is generally understood in the art, a stylus member 168 can be used to contact a selected portion, such as a portion of a bone, to move an indicator 170 relative to the scale 166. This can assist in the selection of an apparatus, such as a selected size of a prosthesis for implantation relative to the bone to which the sizing member 140 is used.

The various instruments and prosthesis discussed above can be used according to any appropriate method of implantation or if any appropriate instrument set. The exemplary method discussed herein is only to provide an exemplary method of using and implanting the various prostheses and tools.

Figure 6B:
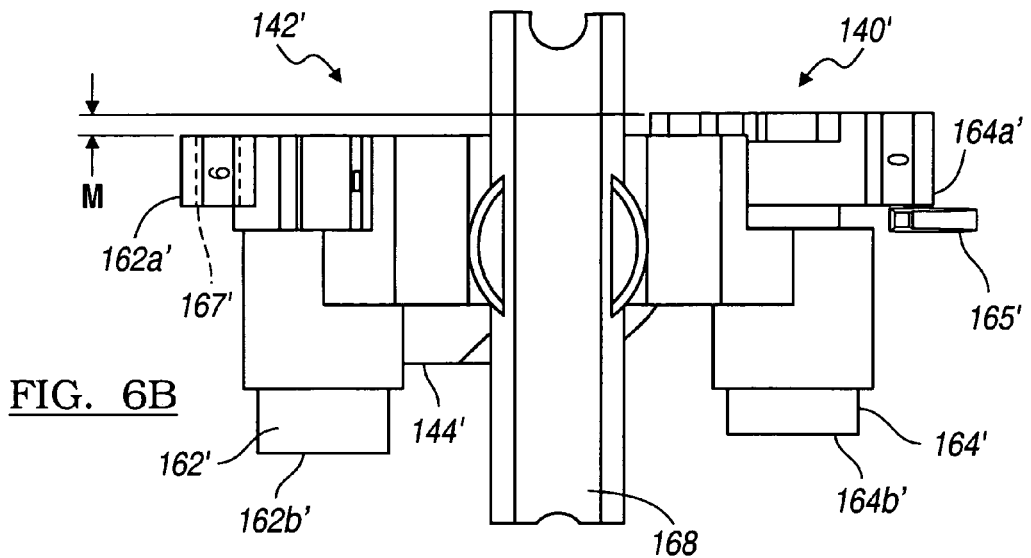
FIG. 6B is a top plan view of an AP sizer according to various embodiments.
Figure 6C:
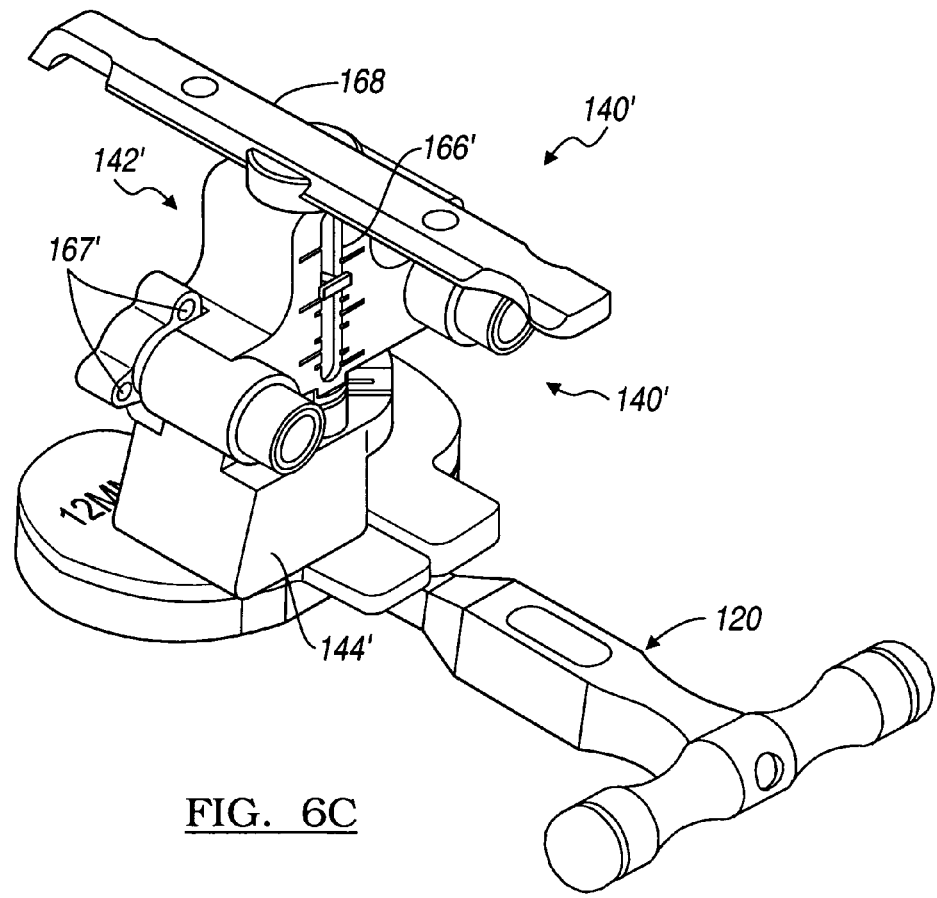
FIG. 6C is a perspective view of an AP sizer associated with a stylus and an alignment tool.

According to various embodiments, the AP sizer 140 can be provided to include various portions. With reference to FIGS. 6B and 6C, an AP sizer 140' is illustrated according to various embodiments. The sizer 140' can be substantially similar to the sizer 140, illustrated in FIG. 6A, and identical portions or substantially similar portions thereto will not be described in detail here. Briefly, the sizer 140' can include the first guide portion 142' and the base portion 144' substantially similar to the first guide portion 142 and base portion 144 discussed above. For example, the base 144' can include a first side that is longer or larger than a second side and the first alignment portion 142' can include a scale 166' that can be used in the sizing procedure. Similarly, the stylus 168 can be provided with the sizer 140' to assist in performing a procedure.

As discussed above, the guide portion 142 can include guide passages 162, 164 that can be used to form holes in a bone, such as a distal portion of the femur. The sizer 140' can include alignment members 162' and 164' that can be substantially similar to the guide passages 162, 164 but can be adjustable. The guide passages 162' and 164' can include a bone contacting portion 162a' and 164a', respectively, and a non-bone contacting or distal portion 162b' and 164b'.

The bone contacting portions 162a' and 164a' can contact the condyles of the femur and assist in aligning the sizer 140' relative to the femur. As discussed further herein, the procedure can include determining an extension gap between the tibia and the femur. If there is a difference between the medial and lateral sides of the femur relative to the tibia in the extension gap, then the guide members 162' and 164' can be appropriately set. For example, with particular reference to FIG. 6B, and assuming that the sizer is positioned relative to a left leg, the medial guide member 164' can be positioned a distance M away from the first alignment portion 142' further than the lateral guide member 162'. Therefore, the medial extension gap is greater than the lateral extension gap. The alignment member 164' can be moved so that the bone engaging portion 164'a engages the bone of the femur in an appropriate manner. This can help ensure that the holes that are being drilled with the alignment or guide bodies 162', 164' are substantially parallel to the mechanical axis of the femur and based upon the difference in the extension gaps.

The alignment members 162', 164' can be moved in any appropriate manner. For example, the alignment members 162', 164' can include external threads while the body portion of the first alignment member 142' includes internal threads to allow for the members 162', 164' to be rotated to achieve an appropriate movement of the guide member 162', 164'. Further, a ratcheting system, a lock system, a spacer clip 165', or the like, can be positioned to assist in holding the selected guide member 162', 164' in an appropriate position relative to the first guide body 142'.

Further, the guide members 162', 164' can include pin holes 167' or a plurality thereof, to assist in holding the guide members 162', 164', relative to the condyles of the femur. It will be understood that this can help assist the maintaining of the position of the sizer 140' relative to the femur, and to the positioning of the guide members 162', 164' relative to the femur. It will be understood, as illustrated particularly in FIG. 6C, that the sizer 140' can be used with the alignment member 120 as discussed further herein. Therefore, it will be understood that the sizers, 140, 140' can be provided according to various embodiments to achieve a selected result. Further, the sizer 140' can be used in any appropriate manner, such as that discussed relative and with the sizer 140.

Figure 7:
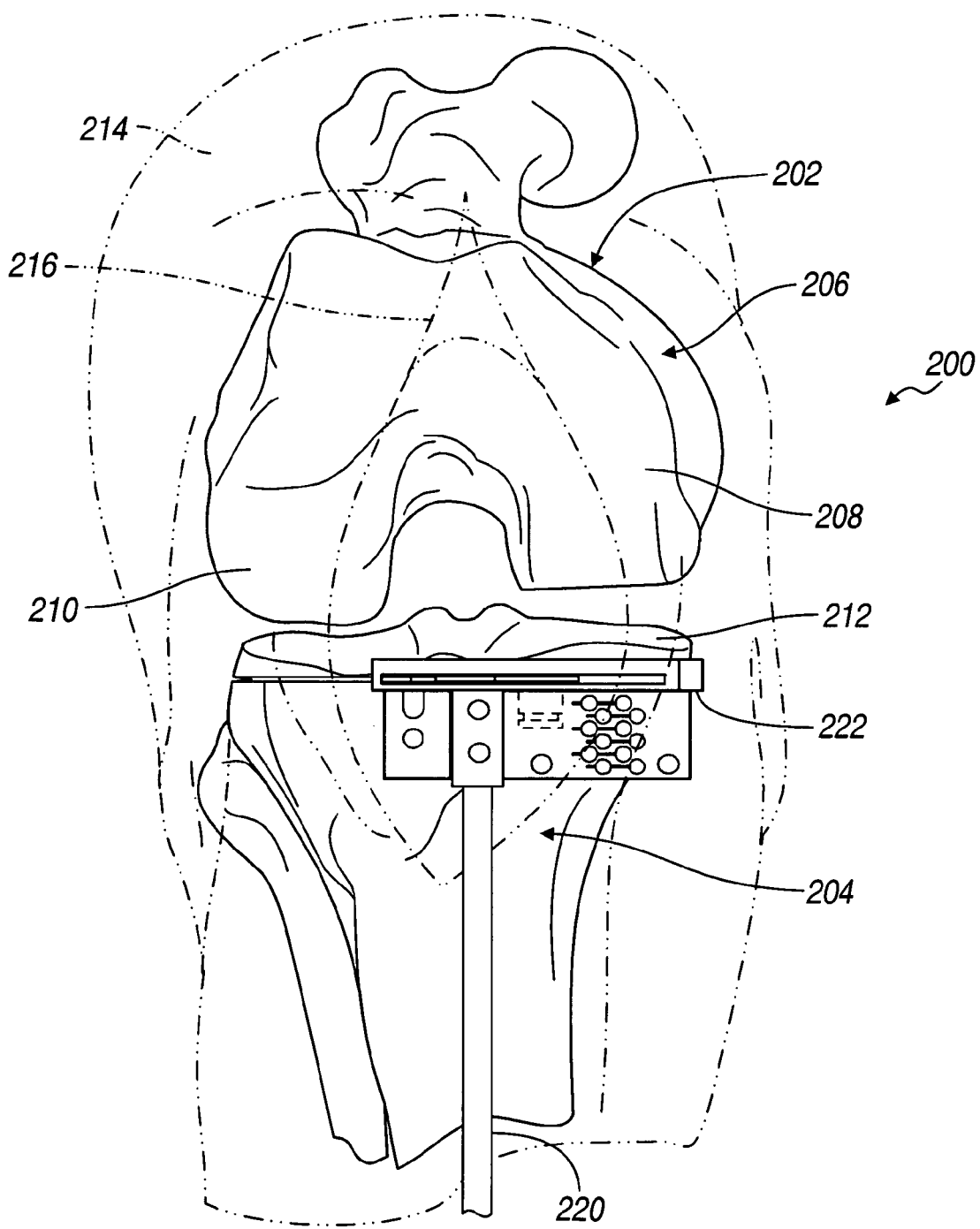
FIG. 7 is an environmental view of a portion of an anatomy and a guiding instrument.

With reference to FIG. 7, a portion of an anatomy, such as a knee portion 200 is illustrated. The knee portion can generally include a femur 202 and a tibia 204, a distal portion 206 of the femur can include a first condyle 208 and a second condyle 210. The first and second condyles 208, 210 can be any appropriate condyles, such as a medial and lateral condyle. As illustrated here, the first condyle 208 is a medial condyle while the second condyle 210 is a lateral condyle. Although the following exemplary discussion can relate to a medial lateral condyle, it will be understood that the various instruments and prostheses can be used for any appropriate procedure and the first and second condyles can also be a lateral and medial condyle respectively.

The tibia 204 can include a proximal portion of the tibia 212 that can be resected according to any appropriate method. Also, the knee 200 is generally surrounded by soft tissue 214. The soft tissue can include adipose tissue, muscle, connective tissue, or any appropriate tissue. The soft tissue 214 can be entered by forming an incision 216 in the soft tissue. The incision 216 in the soft tissue 214 can allow access to the bones, such as the femur 202 and the tibia 204 to perform a procedure relative thereto.

The tibia 204 can be resected in any appropriate manner such as milling or cutting. For example, an external rod 220 can be interconnected with a guide member 222 to perform a resection of the proximal tibia 212. The guide member 222 can be interconnected with the rod 220 in any appropriate manner. Further, the rod 220 can be interconnected with a selected instrument or a portion of the anatomy, such as with an ankle clamp. It will be understood that the rod 220 and the guide 220 can be used according to any appropriate method, such as those generally known in the art.

Figure 8:
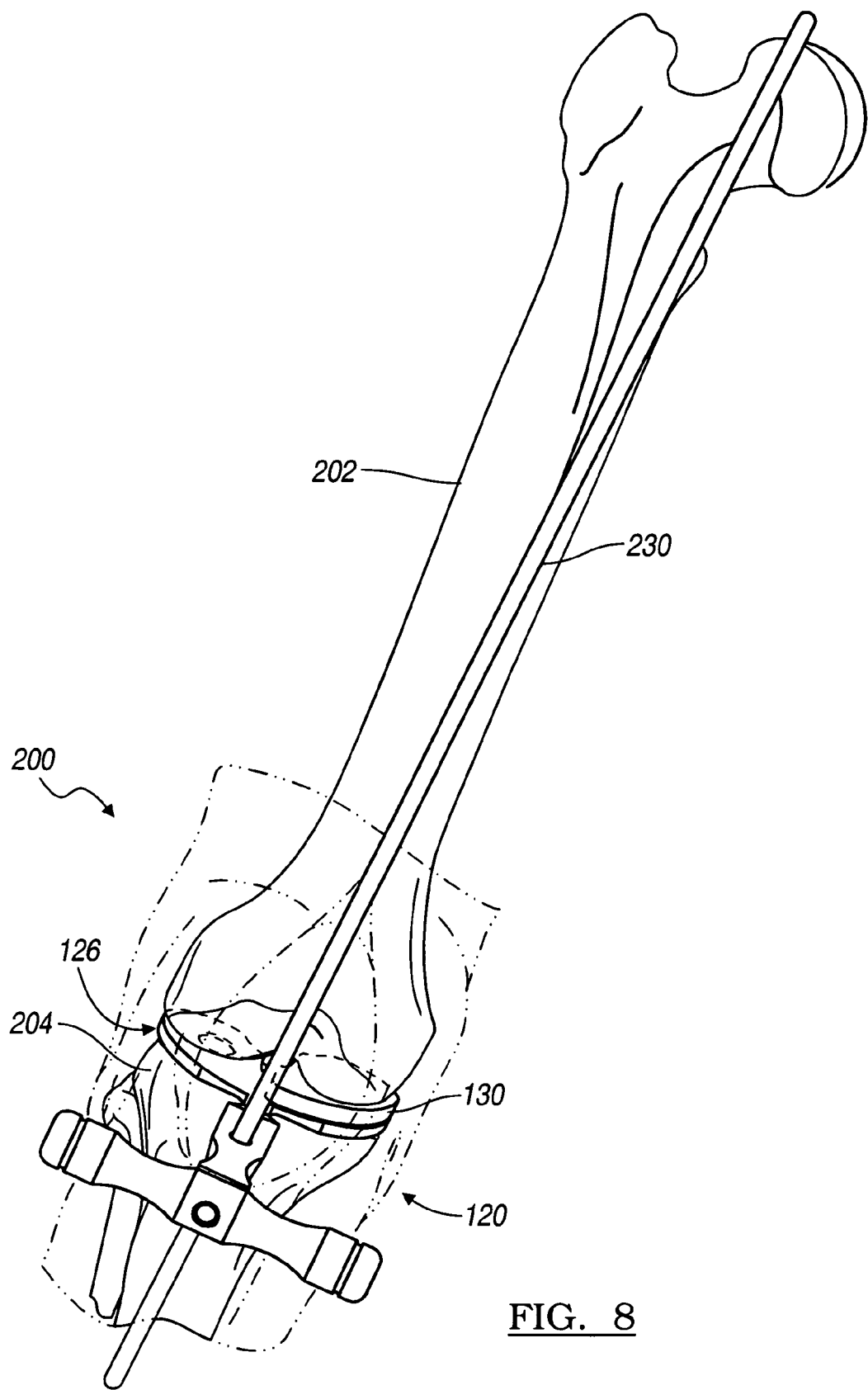
FIG. 8 is an environmental view of an alignment instrument of various embodiments.

With reference to FIG. 8, once the tibia 204 has been resected, at least in the first instance, the alignment instruments 120 can be positioned between the tibia 204 and the femur 202 when the knee 200 is in extension. The alignment tool 120 can be positioned between the femur and the tibia 202, 204 to ensure an appropriate distance or soft tissue tension between the two bones. It will be understood that the spacer members 130 can be positioned relative to the alignment tray 126 to ensure an appropriate contact between the femur 202 and the alignment tool 120 when it is positioned between the two bones. It will be understood that if the alignment tray 126 cannot be positioned between the tibia 204 and the femur 202, a further amount of the tibia 204 can be resected. Nevertheless, the spacers 130 can ensure, after an initial resection of the tibia 204, that the alignment tool 120 can contact both of the condyles of the femur 202 and the resected portion of the tibia 204.

With the alignment tool 120 positioned between the femur 202 and the tibia 204, a varus/valgus alignment rod 230 can be inserted through the passage 132 defined by the alignment tool 120. If the varus/valgus alignment rod 230 aligns or passes through a femoral head 232, generally formed at an proximal end of the femur 202, an appropriate varus/valgus angle has been achieved. It will be understood, however, that if the varus/valgus alignment rod 230 does not intersect or become aligned with the femoral head 232, that various soft tissue releases can be performed to achieve the appropriate alignment of the femur 202 and the tibia 204. It will be understood that soft tissue releases can be performed in any manner, such as those generally understood in the art.

Figure 9:
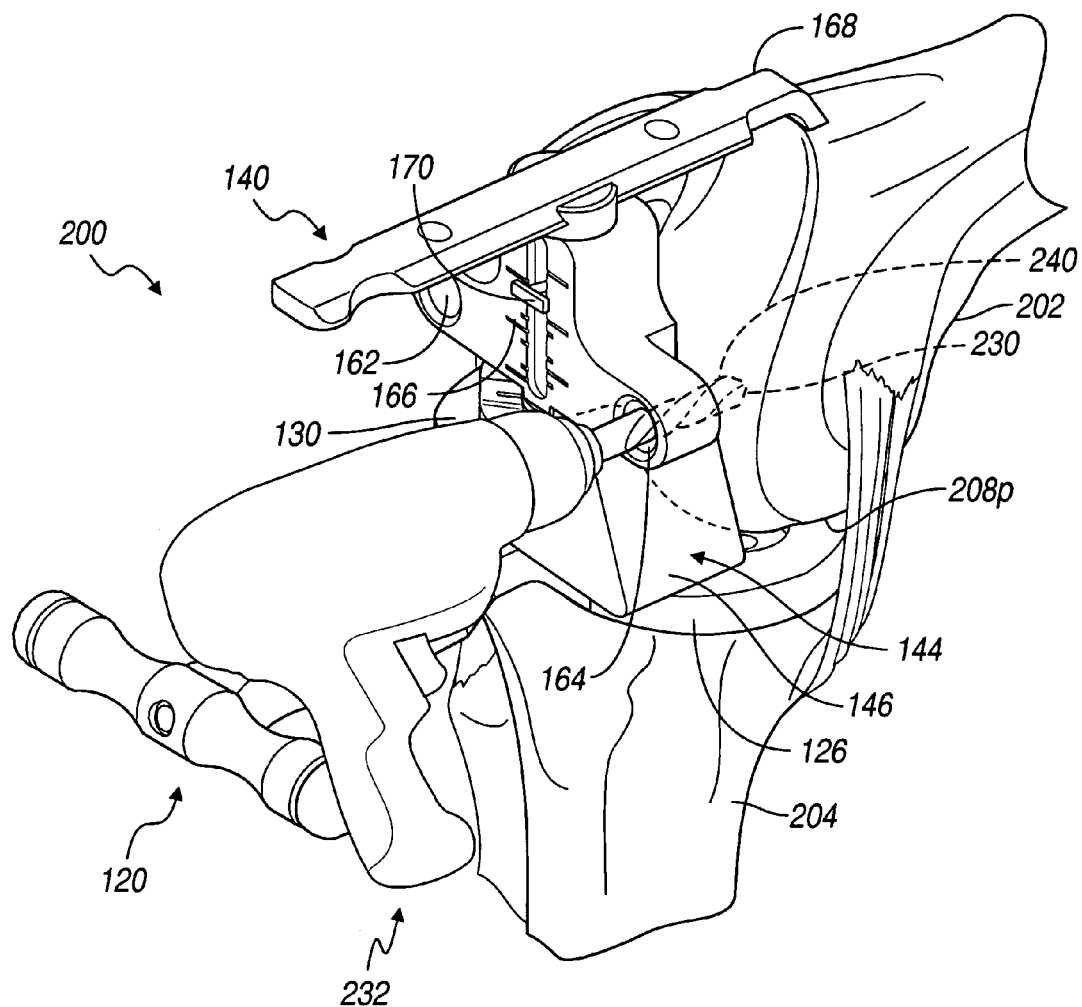
FIG. 9 is an environmental view of a sizing instrument and a section instrument according to various embodiments.
Figure 10:
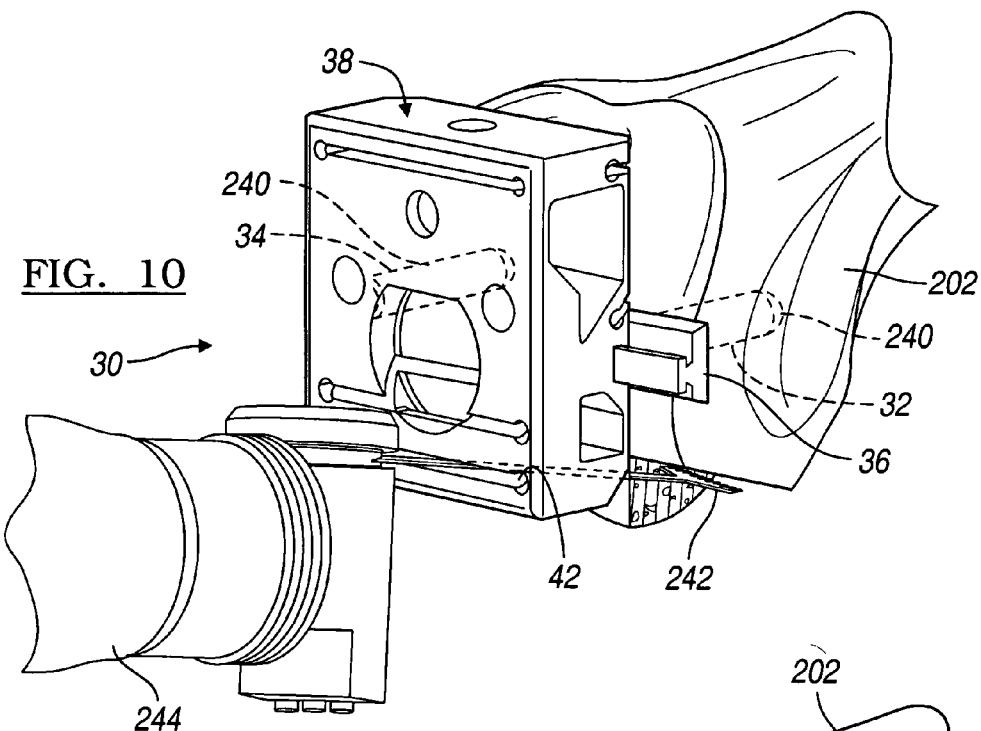
FIG. 10 is an environmental view of a guide block and a saw blade according to various embodiments.

Once the appropriate varus/valgus alignment has been achieved, the knee 200 can be moved into flexion, wherein the tibia is positioned at an angle relative to the femur 202. With the knee in flexion, as illustrated in FIG. 9, the alignment tool 120 can be repositioned relative to the femur 202 and the tibia 204. With the knee in flexion and the alignment tool 120 positioned on the resected proximal portion of the tibia 204, the alignment tool 120, in particular the alignment surface 126, is operable to contact a posterior portion of the first condyle 208p and the posterior portion of the second condyle 210p. It will be understood that if the alignment surface 126 cannot fit between the posterior condyles 208p 210p in a resected surface of the tibia 204, that further resection of the tibia 204 can be performed. Further, as discussed above, various of the spacer blocks 130 can be interconnected with the alignment tray 126 to ensure a proper fit of the alignment tool 120 relative to the femur 202 and the tibia 204. Any appropriate height or dimension of the spacer blocks 130 can be achieved by interconnecting a selected one of the spacer blocks with the alignment tray 126. Therefore, a greater or lesser alignment block can be used to achieve an appropriate contact. Generally, a user can select the pressure or the firmness of contact between the various bone portions and the alignment tray 126 or the selected spacers 130.

Once the appropriate contact has been achieved between the alignment instrument 120 and the femur 202 and the tibia 204, the sizer 140 can be placed relative to the alignment instrument 120. It will be understood that the sizer 140 can be positioned relative to the alignment instrument 120 in any appropriate manner. For example, a connecting mechanism, including a lock, a magnet, or the like, can assist in holding the sizing instrument 140 relative to the alignment instrument 120. Further, the base 144 of the sizing instrument 140 can contact the various portions of the alignment tray 126 and any spacers 130 that may be present. Nevertheless, the taller or larger side 146 of the base 144 contacts the lowest side of the alignment instrument 120 so that references can always be taken off the lowest side. It will be understood, however, that reference can be taken relative to any appropriate portion of the alignment tool 126 and that referencing from the lower side of the alignment tool 120 is merely exemplary.

Once the sizing instrument 140 has contacted the alignment tray 126, the stylus 168 can contact the selected portion of the femur 202, such as a proximal anterior surface thereof. The stylus 168 can contact the anterior surface of the femur 202 so that the marker 170 is positioned relative to the scale 166 to assist in selecting appropriate prosthesis size. The appropriate size can be determined based upon the scale 166 and can be any appropriate size. It will be understood that the prostheses 60, 90 can be provided in a plurality of sizes and can be provided in a kit, including a plurality of sizes, to be selected based upon the sizer 140. Nevertheless, it will be understood that any appropriate mechanism or method can be used to select the appropriate size of the prosthesis, such as user experience, other measuring or sizing tools.

Further, the guide holes 162, 164 can be used to assist in forming bores 240 within the condyles 208, 210 of the femur 202. Any appropriate tool, such as a drill point 230 interconnected with a drill motor 232 can be used to form the bores in the femur 202. The drill point 230 can be guided through the guide bores 162, 164 to form the bores 240 within the femur 202 and appropriate positions relative to the posterior surfaces 208p, 210p of condyles 208, 210. Once the bores are formed in the femur 202, the alignment apparatus 120 and the sizer apparatus 140 can be removed from the knee 200.

Once the alignment 120 and the sizer instrument 140 are removed, the three-in-one cutting block 30 can be positioned relative to the femur 202. The holding pegs 32 can be positioned within the formed bores 240 in the femur 202. A resection tool, such as reciprocating saw blade 242 can be powered by a saw motor 244 to form a selected resection of the condyles 208, 210. For example, the guide slot 42 can be used to form a posterior resection of the condyles 208, 210. The resection can be substantially parallel to the guide slot 42 and formed as a substantially flat surface on the posterior portion of the femur 202 relative to the condyles 208, 210. It will be understood, however, that any appropriate resected surface can be formed on the femur 202. Further, it will be understood that the guide portion 38 of the guide assembly 30 can move relative to the rail 36 according to any appropriate mechanism. Various mechanisms and guide portions are described in currently pending and commonly assigned U.S. patent application Ser. No. 11/337,861, filed on Jan. 23, 2006, and incorporated herein by reference. Once the posterior cut is formed with the guide assembly 30, the alignment tool 120 can be used to determine a flexion gap of the knee 200.

Figure 11A:
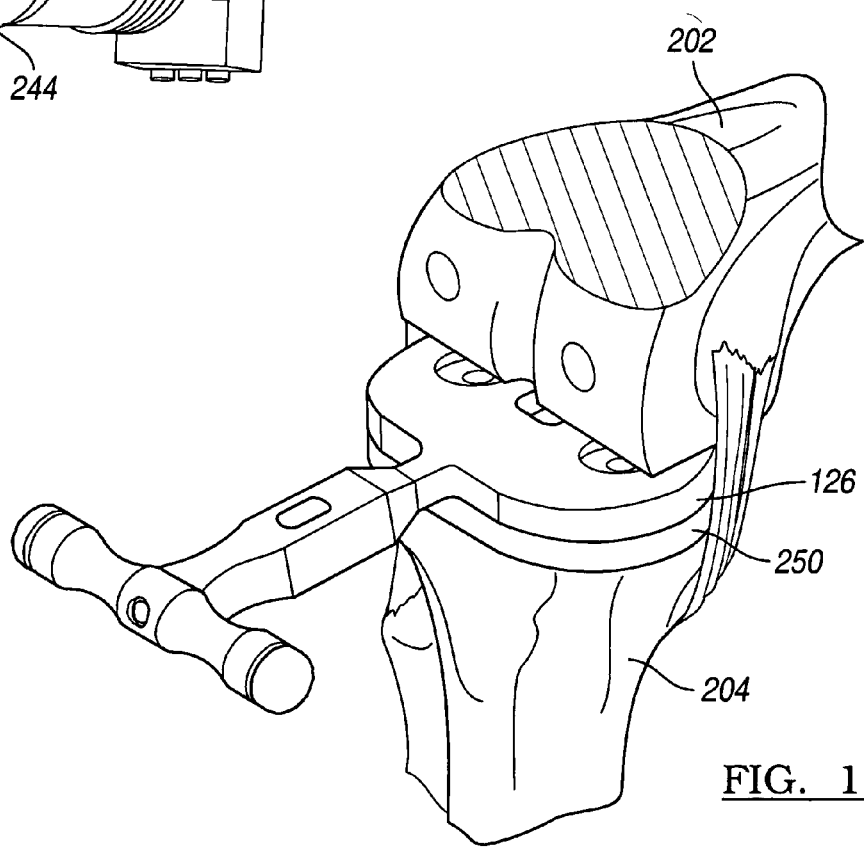
FIG. 11A is an environmental view of an alignment instrument according to various embodiments.

With reference to FIG. 11A, once the posterior resection of the femur 202 is completed, a cut spacer or distal cut spacer 250 can be interconnected with the alignment tray 126 in any appropriate manner. Generally, the cut spacer 250 can be interconnected with the alignment tray 126 on a bottom portion thereof to allow for the connection of the spacers 130 to a top portion of the tray 126 if required. Nevertheless, the cut spacer 250 is connected with the alignment tray 126 to mimic the amount of bone or portion resected due to the resection of the posterior portion of the femur 202.

The cutting block 30 is used to resect a selected amount of the posterior portion of the femur 202. Therefore, the cut spacer 250 can mimic the amount of bone removed and ensure that an appropriate gap is formed between the femur 202 and the tibia 204. The various spacers 130 can also be added to the alignment tray 126 if the selected contact between the femur 202 and the alignment tray 126 is not achieved. In any case, the spacing between the tibia 204 and the femur 202 can be determined with the alignment tool 120. Further, the amount can be noted for use later on. This spacing is generally obtained while the femur 202 is in flexion relative to the tibia 204, as opposed to the extension gap obtained earlier prior to the resection of the femur and immediately after the resection of the tibia 204.

If any of the spacers 130 were required prior to the posterior resection of the femur 202, the smallest spacer size would be interconnected with the alignment tray 126 on both sides relative to both condyles 208, 210 during the flexion gap measurement. If no spacer were used on one side relative to one of the condyles 208, 210, then no spaces would be used relative to the alignment tray 126 when determining the flexion gap. It will be understood that the flexion gap can generally be determined once the posterior resection of the condyles 208p, 210p has occurred.

Figure 11B:
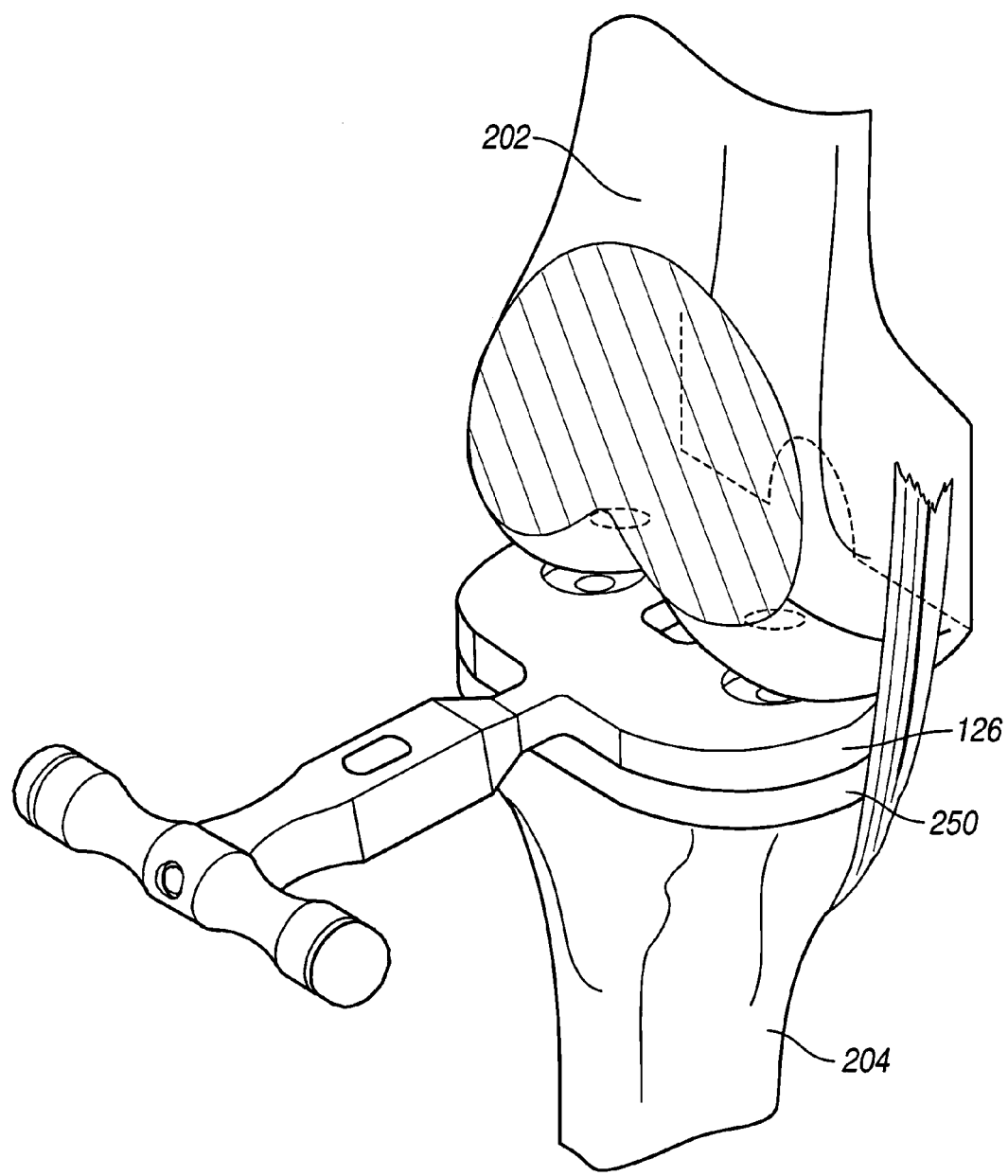
FIG. 11B is an environmental view of an alignment instrument in a knee while in extension.

Also, in addition to the earlier extension gap determination, the extension gap can be re-determined as illustrated in FIG. 11B. With the knee 200 in extension, the alignment tray 126, without the cut spacer 250, can be reinserted between the femur and the tibia where the knee 200 is in extension. The spacers 130 can be interconnected with the alignment tray 126, if necessary, to provide a tight fit between the tibia 204 and the femur 202 with the alignment tool 120. The gap in extension can thus be determined.

The extension gap can then be subtracted from the flexion gap to determine a length for the spigot 12. The spigot 12 can include a length or guide portion that is substantially equal to the difference between the extension gap and the flexion gap to ensure that only an appropriate amount of the femur 202 is resected. It will be understood that the spigot 12 can be provided in appropriate sizes, such as in about 2 mm differences, to ensure that the amount resected with the mill 14 is an appropriate amount guided by the spigot 12. Nevertheless, once the difference in gap is determined, the appropriate spigot can be determined. Also, it will be understood, that the difference between the condyles 208, 210 can be the same or not be the same; therefore, the spigot 12 used for each of the condyles 208, 210 can be different.

Figure 12:
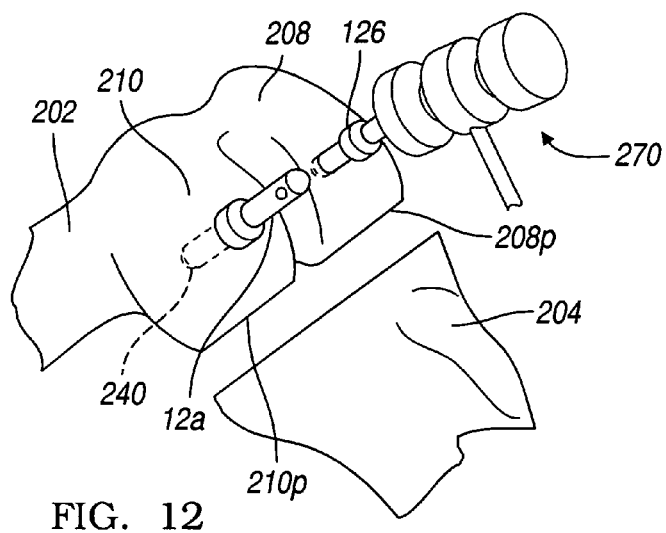
FIG. 12 is an environmental view of a guide instrument relative to an anatomy.
Figure 13A:
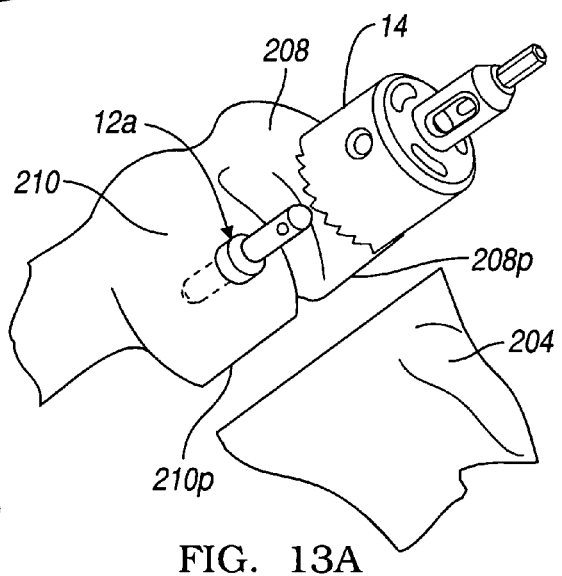
FIG. 13a is an environmental view of a resection guide and a resection instrument relative to an anatomy. According to various embodiments.
Figure 13B:
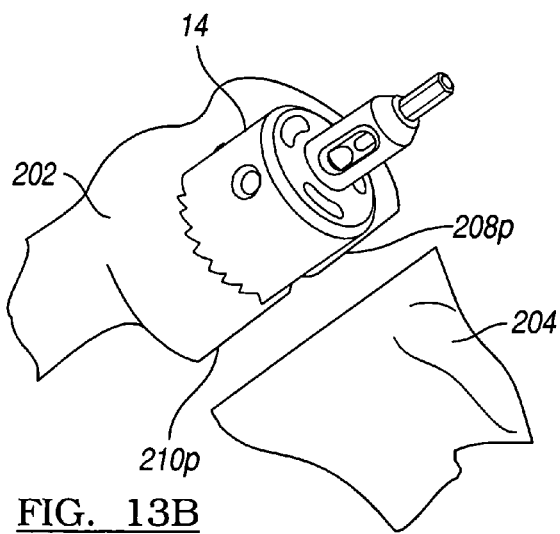
FIG. 13b is an environmental view of a resection instrument relative to an anatomy according to various embodiments.

With reference to FIG. 12, once the appropriate spigots are determined, they can be inserted into the bores 240 defined in the condyles 208, 210. Any appropriate instrument or tool, such as the hammer 270, can be used to insert the spigots 12 into the condyles 208, 210. It will be understood that different size spigots can be used, such as a first spigot 12a and a second spigot 12b. Therefore, the femur 202 can be resected in the appropriate manner with the mill 14 illustrated in FIG. 13, to achieve a selected amount of resection of the femur 202.

Further, it will be understood, that the mill 14 can provide a substantially spherical surface on the condyles 208, 210. The spherical or curved surface on the condyles 208, 210 can mate with any appropriate implant, such as the prosthesis 60, or the prosthesis 90. Although the resection can be any appropriate shape.

Figure 14:
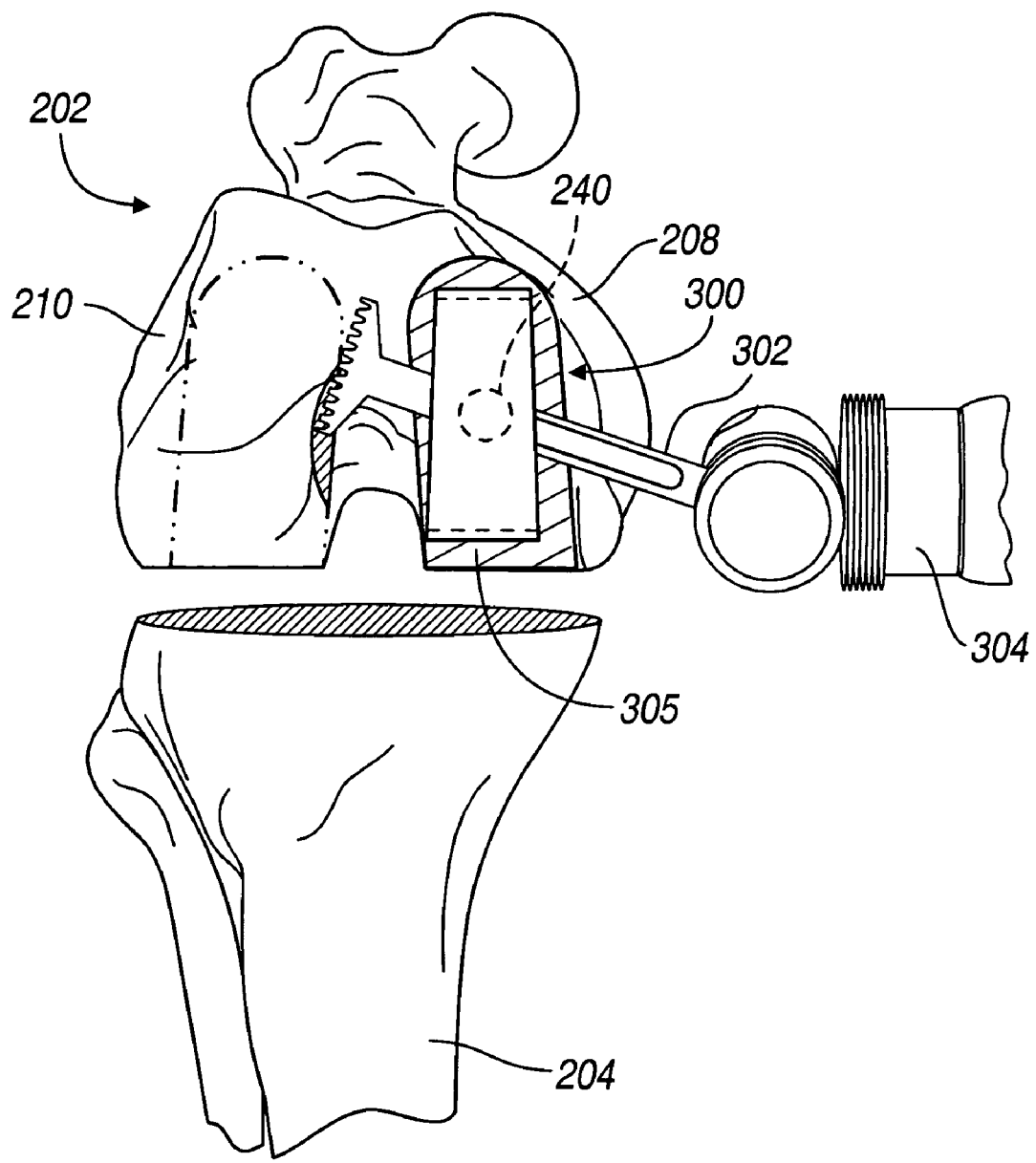
FIG. 14 is an environmental view of a resection instrument relative to a portion of the anatomy according to various embodiments.

In addition to providing the spigot 12a, 12b to guide the mill 14 relative to each of the condyles 208, 210, a second mechanism can, alternatively or in addition, be used to resect a second or adjacent condyle. For example, with reference to FIG. 14, a resection guide 300 can be positioned relative to the bore 240 formed in one of the condyles, such as the condyle 208. The resection guide 300 can include a guide slot to guide a saw blade 302 relative to the second condyle 210. The saw blade 302 can be powered by any appropriate instrument, such as a saw motor 304. The saw motor 304 can move the saw 302 in a substantially reciprocating or vibrating fashion. Therefore, the saw blade 302 can cut the second condyle 210 relative to the bore 240 formed in the first condyle 208. The first condyle 208 can be first resected with the mill 14 or the second condyle 210 can be resected prior to the resection of the first condyle 208.

According to various embodiments, the saw guide 300 can be positioned relative to the milled surface 304 of the first condyle 208 so that the saw guide 300 is positioned at the resected surface or depth of the first condyle 208. Therefore, the saw 302 can be moved relative to the second condyle 210 to form a resection that is substantially aligned with the resection 304 of the first condyle 208. This can allow for the femur 202 to be resected in a manner that is appropriate to position a prosthesis, such as the prosthesis 90. It will be understood that the cut surface 304 formed with the mill 14 can be curved in a selected manner while the surface of the second condyle 210 resected with the saw can be substantially flat. Therefore, the prosthesis 90 that includes both a flat distal portion and a substantial curved distal portion which can mate with the resected portions of the femur 202 resected with the mill and the saw blade. It will be understood, however, that the femur, including the condyles 208, 210 can be resected in any appropriate manner.

Once the initial resection of the distal portion of the condyles 208, 210 is completed, the various guides, such as the spigot 12 or the saw guide 300 can be removed. Previous extraneous portions of bone can be removed in any appropriate manner, such as with a Rongeur, an ostephyte chisel, or any other appropriate tool. It is understood by one skilled in the art that the resected surface of the femur 202 can be prepared in any appropriate manner to allow for implantation of a prosthesis, such as the prosthesis 60 or the prosthesis 90.

Once the resection guides are removed, the cut spacer 250 can be reconnected or connected with the alignment tool 120 and positioned between the femur 202 and the tibia 204 with the knee 200 in extension. This can be done to ensure that an appropriate extension gap is created prior to positioning the implant or prosthesis portions or trial prosthesis portions into the knee 200. If the appropriate extension gap has not been achieved, as determined by any appropriate means such as the alignment tool 120, additional material from the bone, such as the femur 202, can be resected. This can be repeated until an appropriate amount of the femur 202 has been resected to achieve an appropriate gap.

Figure 15:
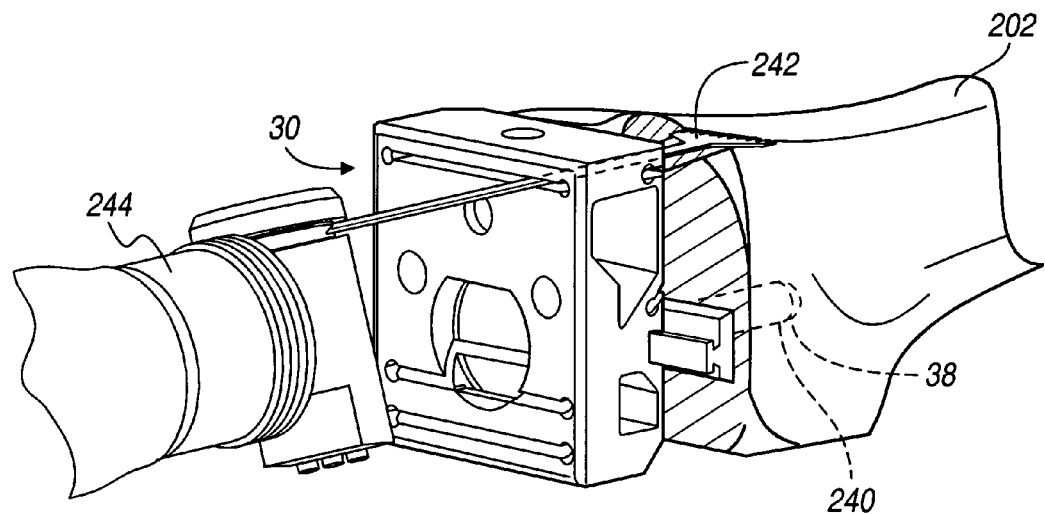
FIG. 15 is an environmental view of a resection instrument and resection guide relative to an anatomy according to various embodiments.

Once the appropriate extension gap has been achieved, the resection guide or cutting block 30 can be reconnected with the femur 202 with use of the bores 240 as illustrated in FIG. 15. The cutting guide 30 can be used to form an anterior resection of the femur 202 and an anterior chamfer cut of the femur 202. It will be understood, by one skilled in the art, that these cuts may be typical for resecting the femur 202 to allow for implantation of a selected distal femoral prosthesis. Any appropriate tool can be used to form the resection, such as the saw blade 242 and the saw motor 244. A user, such as a surgeon, can use the saw 242 and saw motor 244 to resect portions of the femur 202 using the cutting guide 30. As discussed above, the cutting guide 30 can move relative to the femur 202 on the rail, as illustrated in FIG. 15.

Figure 16:
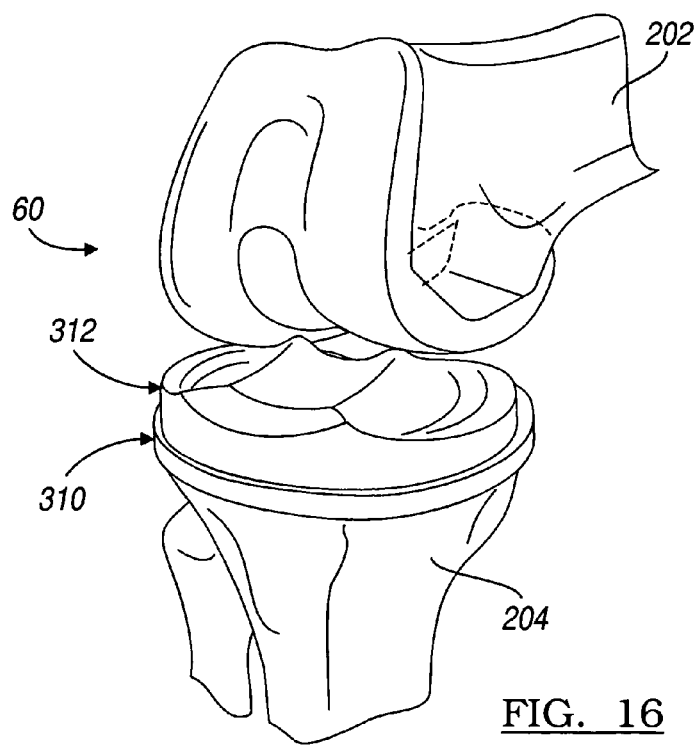
FIG. 16 is an environmental view of a prosthesis positioned relative to a selected portion of an anatomy.

Once the final portions of the femur are resected with the guide 30, the implant, such as the implant 60 or the implant 90, or any other appropriate prosthesis or implant can be positioned relative to the resected portion of the femur 202 as illustrated in FIG. 16. As discussed above, the prosthesis can include various portions such as smooth surfaces, roughened surfaces, porous coated surfaces, or the like to allow or assist with fixation of the prosthesis 60, 90 relative to the femur 202. Also, other prosthesis members can be positioned, such as a tibial member 310 and a bearing 312. These can be any appropriate portions such as those generally known in the art. Though any prosthesis members may be used, such as more bearing members or no bearing members.

Therefore, a user, such as a surgeon, can decide to use an adhesive such as bone cement (e.g. polymethylmethacrylate) or any appropriate material. Alternatively, a user can decide to implant the prosthesis using no adhesive to allow for bone ingrowth over a selected period of time. Further, the various prostheses can first be trials positioned relative to the resected portions of the femur 202 and the tibia 204. The trials can ensure an appropriate fit of the prosthesis relative to the resected portions of the femur and the tibia. The trialing can also determine whether additional resection may be necessary to achieve an appropriate fit. Nevertheless, the use of the various instruments, such as the sizer 140, can assist in ensuring the appropriate size selection for the prosthesis. As discussed above, the kits or a kit can include a plurality of the prosthesis members of different sizes, including heights, thicknesses, widths, and the like to achieve an appropriate fit with the femur of the patient.

Further, one skilled in the art will understand that the use of the various prosthesis, instruments, and the like, can allow for the incision 216 can be about 2 cm to about 10 cm, such as about 4 cm to about 8 cm. The incision 216 can be formed by a user according to any appropriate purpose, such as achieving appropriate visualization of the internal anatomy, including the femur 202 and the tibia 204 or minimizing trauma to a patient. Nevertheless, the mill 14 can be passed and operated through substantially small incision, such as that generally known in the art such as the procedure and use for the Oxford® Unicompartmental Knee Implant™ instrumentation provided by Biomet, Inc. of Warsaw, Ind. The procedure here, however, can allow for positioning to complete distal femoral prosthesis. This can generally be assisted by resecting only a selected one of the condyles 208, 210 at a time. The instrumentation allows for guiding a selected resection instrument relative to a single one of the condyles 208, 210, if selected. Nevertheless, the resections of both of the condyles 208, 210 can be substantially aligned or achieved in an appropriate manner by allowing the selected resections to be formed relative to one another in a substantially aligned manner. Therefore, the condyles 208, 210 can be resected separately and still be substantially aligned for use of implantation of a selected prosthesis.

As discussed above, various prosthesis members can be provided according to various embodiments. For example, with reference to FIG. 17, a posterior stabilized (PS) knee implant or a substantially constrained or hinged knee prosthesis can be provided. Although a PS stabilized knee or a constrained knee can provide for greater stability in a knee prosthesis, the prostheses can include various features as discussed above.

Figure 17:
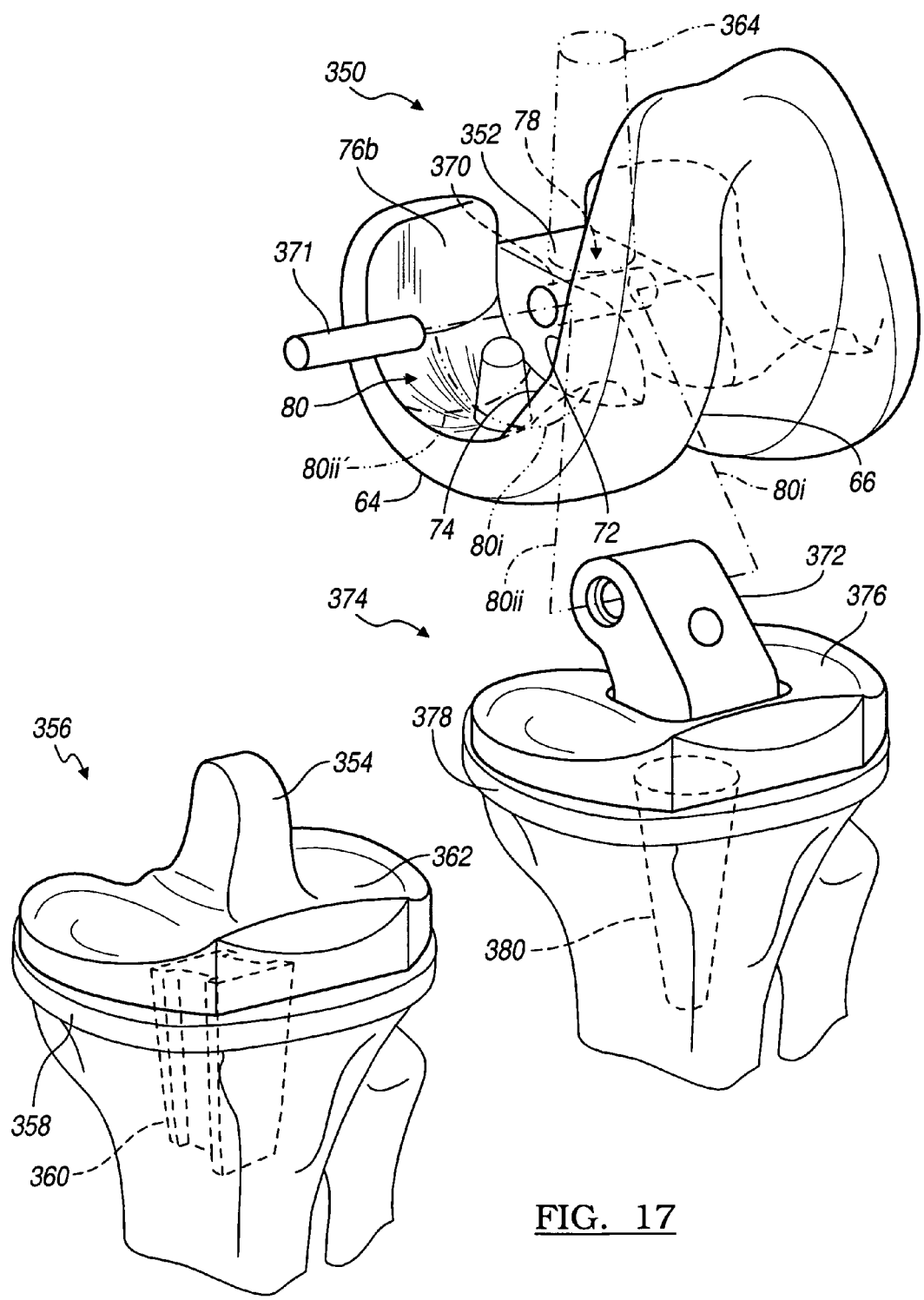
FIG. 17 is a prosthesis according to various embodiments.

With reference to FIG. 17, a distal femoral prosthesis 350 is illustrated. The prosthesis 350 can include the portions that are substantially similar to the prosthesis 60 and similar numerals are used to reference the similar portions. For example, the prosthesis 350 can include a first curved interior surface 78 and a second curved interior surface 80. The curved interior surfaces 78, 80 can be substantially similar to the curved surfaces discussed above in relation to the prosthesis 60 including the various arcs, radii, and curvatures as illustrated in FIGS. 3A-3D. Further, an exterior surface 66, such as a patella track, can be provided.

Although the interior portion of the prosthesis 350 can include various planar portions, such as an anterior planar portion 72, an anterior chamfer planar portion 74, and posterior planar portions 76a, 76b, in conjunction with the curved surfaces 78, 80; it can also include an internal structure, such as a stabilizing structure 352. The stabilizing structure 352 can include any appropriate posterior stabilizing structure, such as those generally known in the art including those provided in the Maxim® knee prosthesis provided by Biomet, Inc. of Warsaw, Ind. The stabilizing structure can be a posterior stabilizing box 352 that can cooperate with a posterior stabilizing post 354 of an appropriate tibial component 356. The tibial component 356 can include a tibial tray 358 that is able to engage a selected anatomical portion, such as the tibia 204. A stem or boss 360 can be provided to engage the tibia 204 in a selected manner, such as to reduce rotation of the tibial component 356 after implantation. It will be understood that various methods and apparatuses can be used to implant, fix, etc., the tibial component 356 relative to the tibia 204.

A bearing component 362 can incorporate the posterior stabilizing post 354 or the posterior stabilizing post 354 can be provided separate from the bearing component 362 as a single member with the tibial tray 358, or in any appropriate combination. Nevertheless, one skilled in the art will understand that the posterior stabilizing post 354 can interconnect with the stabilizing box 352, also known as an intercondylar box 352, to assist in stabilizing the femur 202 relative to the tibia 204 after implantation of the prosthesis 350.

Further, the prosthesis 350 can include various components, such as an intramedullary post or stem 364 to assist in interconnection or fixation of the prosthesis relative to the femur 202. It will be understood that any other appropriate portions, such as the projections 84, 86, can also be provided to assist in fixation of the prosthesis 350 relative to the femur 202. It is further understood that the intramedullary stem 364 is merely exemplary and can be provided or not provided in various fashions, such as a modular stem.

In addition, the intercondylar box 352, or other appropriate structure, can provide a passage 370 that can interconnect with a pin 371 or other axle of a hinged stem 372 of a tibial component 374. It will be understood that either of the tibial component 356 or the tibial component 374 can be provided in various combinations with the prosthesis 350 according to the decision by a user, the physical aspects of the patient, or in any selected combination to achieve a selected result. It will be understood that the prosthesis 350 can include any appropriate portions to allow for interconnection with the tibial prosthesis 356 or the tibial prosthesis 374.

The tibial prosthesis 374, however, can also generally include a bearing portion 376 that can be provided relative to a tibial tray 378 that can include a boss or a stem 380 that can be interconnected with the tibia 204. Again, it is understood by one skilled in the art that the method and implantation process of the tibial stem 374 such as the OSS™ Orthopaedic Salvage System knee provided by Biomet, Inc. of Warsaw, Ind.

Therefore, it will be understood that the prosthesis 350, that can include one or two curved surfaces to contact a selected portion of the anatomy, such as the femur. While the prostheses 60, 90, can generally understood to be cruciate retaining prostheses, other types such as a posterior stabilized or constrained knee prosthesis, such as the prosthesis 350, can be provided to interconnect with the femur 202. These various types of knee prostheses can also include fixed or floating bearing members or no bearing members. Also, the prostheses can be primary or revision prostheses. One skilled in the art will understand that the selection of the appropriate prosthesis can be made by a user for implantation relative to a patient. Nevertheless, the various curved or flat surfaces can be provided in any appropriate combination for any appropriate prosthesis type for implantation into an anatomy.

What is claimed is:

1. A prosthesis for positioning in a selected portion of an anatomy, the prosthesis comprising:
    a first portion defining a substantially planar surface operable to fixedly engage a first surface of the anatomy;
    a chamfer portion defining a substantially planar surface extending at a positive angle from the substantially planar surface defined by the first portion, the chamfer portion operable to engage a chamfer surface of the anatomy;
    a second portion defining a curved surface operable to engage a second surface of the anatomy, the curved surface having a first radius that forms a first arc that intersects with a second radius that forms a second arc; and
    a third portion defining a substantially planar surface operable to fixedly engage a third surface of the anatomy, the curved surface defined by the second portion between the chamfer portion and the third portion.

2. The prosthesis of claim 1, wherein the first portion and the second portion are formed from a single member.

3. The prosthesis of claim 1, further comprising:
    wherein at least one of the substantially planar surface defined by the first portion, the curved surface defined by the second portion, and the substantially planar surface defined by the third portion is formed at an angle relative to another of the substantially planar surface defined by the first portion, the curved surface defined by the second portion, and the substantially planar surface defined by the third portion.

4. The prosthesis of claim 1, further comprising:
    a member extending from the curved surface defined by the second portion.

5. The prosthesis of claim 1, further comprising:
    an exterior surface on a side opposite the first portion and the second portion.

6. The prosthesis of claim 5, wherein the exterior surface defines a distal femoral articular surface, a proximal tibial articular surface, a distal humeral surface, or combinations thereof.

7. The prosthesis of claim 1, wherein the prosthesis is a distal femoral prosthesis;
    wherein the second portion is operable to engage a distal portion of the femur of the anatomy.

8. The prosthesis of claim 1, wherein the curved surface defines a bone contacting surface operable to engage a distal portion of a femur wherein the distal portion of the femur can be prepared to include a substantially curved surface to be contacted by the curved surface defined by the second portion.

9. The prosthesis of claim 3, wherein the first portion defines an anterior portion of the distal femoral prosthesis, the chamfer portion defines an anterior chamfer portion of the distal femoral prosthesis, the third portion defines a posterior portion of a distal femoral prosthesis, and the second portion defines a distal portion of a distal femoral prosthesis.

10. The prosthesis of claim 1, further comprising:
    a fourth portion defining a second curved surface operable to engage a fourth surface of the anatomy;
    wherein the second portion and the fourth portion are operable to be placed relative to resected condyles of a femur.

11. A distal femoral prosthesis for positioning on a distal end of a femur, the distal femoral prosthesis comprising:
    a lateral condyle portion;
    a medial condyle portion; and
    a patella track portion;
    wherein the lateral condyle portion, the medial condyle portion, and the patella track portion includes an exterior articulating surface and an interior bone-engaging surface
    wherein the exterior articulating surface includes an anterior patella track articulating surface, a lateral condyle articulating surface and a medial condyle articulating surface;
    wherein the interior bone-engaging surface includes a planar anterior bone-engaging surface, a planar anterior chamfer bone-engaging surface extending at an angle from the planar anterior bone-engaging surface, a planar posterior bone-engaging surface, and a curved distal condyle bone-engaging surface between the planar anterior chamfer bone-engaging surface and the planar posterior bone-engaging surface;

wherein the curved distal condyle bone-engaging surface includes at least a first curved bone-engaging surface formed opposite the lateral condyle articulating surface or the medial condyle articulating surface where the first curved bone-engaging surface includes a substantially anterior-to-posterior curvature having a first radius that forms a first arc and a substantially medial-to-lateral curvature having a second radius that forms a second arc.

12. The distal femoral prosthesis of claim 11, wherein the curved distal condyle bone-engaging surface includes a second curved bone-engaging surface formed opposite the other of the lateral condyle articulating surface or the medial condyle articulating surface where the second curved bone-engaging surface includes a substantially anterior-to-posterior curvature having a third radius that forms a third arc and a substantially medial-to-lateral curvature having a fourth radius that forms a fourth arc.

13. The distal femoral prosthesis of claim 12, further comprising a first projection extending from the first curved bone-engaging surface and a second projection extending from the second curved bone-engaging surface.

14. A distal femoral prosthesis for positioning in a distal portion of a femur, the distal femoral prosthesis comprising:
   an anterior portion defining a substantially planar surface operable to fixedly engage an anterior surface of the femur;
   an anterior chamfer portion defining a substantially planar surface extending at a positive angle from the substantially planar surface defined by the anterior portion, the anterior chamfer portion operable to engage an anterior chamfer surface of the femur;
   a distal portion defining a curved surface operable to engage a distal surface of the femur, the curved surface includes a substantially anterior-to-posterior curvature having a first radius that forms a first arc and a substantially medial-to-lateral curvature having a second radius that forms a second arc; and
   a posterior portion defining a substantially planar surface operable to fixedly engage a posterior surface of the femur, the curved surface defined by the distal portion between the anterior chamfer portion and the posterior portion.

15. The distal femoral prosthesis of claim 14, further comprising a first condyle portion and a second condyle portion, and wherein the anterior portion, the anterior chamfer portion, the distal portion, and the posterior portion are included on at least one of the first condyle portion and the second condyle portion.

16. A prosthesis for positioning in a selected portion of an anatomy, the prosthesis comprising:
   a first portion defining a substantially planar surface operable to fixedly engage a first surface of the anatomy;
   a second portion defining a curved surface operable to engage a second surface of the anatomy, the curved surface having a first radius that forms a first arc and a second radius that forms a second arc, the first and second radii being different from each other, and the first and second arcs being substantially perpendicular to each other; and
   a third portion defining a substantially planar surface operable to fixedly engage a third surface of the anatomy, the curved surface defined by the second portion between the first portion and the third portion.

* * * * *